(12) United States Patent
Duggal et al.

(10) Patent No.: US 8,470,013 B2
(45) Date of Patent: Jun. 25, 2013

(54) SYSTEMS AND METHODS FOR ANEURYSM TREATMENT AND VESSEL OCCLUSION

(75) Inventors: Neil Duggal, London (CA); Robert John De Hoog, London (CA); Donald H. Lee, London (CA); Louise C. Raymond, London (CA); Joshua A. Butters, Chandler, AZ (US)

(73) Assignees: IMDS Corporation, Providence, UT (US); Neil Duggal, London, Ontario (CA)

( * ) Notice: Subject to any disclaimer, the term of this patent is extended or adjusted under 35 U.S.C. 154(b) by 227 days.

(21) Appl. No.: 12/582,052

(22) Filed: Oct. 20, 2009

(65) Prior Publication Data

US 2010/0106240 A1 Apr. 29, 2010

Related U.S. Application Data

(60) Provisional application No. 61/106,670, filed on Oct. 20, 2008, provisional application No. 61/172,856, filed on Apr. 27, 2009.

(51) Int. Cl.
*A61F 2/06* (2006.01)

(52) U.S. Cl.
USPC .......................................... 623/1.1; 623/1.15

(58) Field of Classification Search
USPC ....................................................... 623/1.25
See application file for complete search history.

(56) References Cited

U.S. PATENT DOCUMENTS

| | | |
|---|---|---|
| 4,705,517 A | 11/1987 | DiPisa, Jr. |
| 5,258,042 A | 11/1993 | Mehta |
| 5,464,419 A | 11/1995 | Glastra |
| 5,584,803 A | 12/1996 | Stevens et al. |
| 5,620,461 A | 4/1997 | Muijs Van De Moer |
| 5,645,559 A | 7/1997 | Hachtman |
| 5,662,701 A | 9/1997 | Plaia et al. |
| 5,725,546 A | 3/1998 | Samson |
| 5,749,894 A | 5/1998 | Engelson |
| 5,776,097 A | 7/1998 | Massoud |
| 5,904,146 A | 5/1999 | Plaia et al. |
| 5,904,703 A | 5/1999 | Gilson |
| 5,935,148 A | 8/1999 | Villar et al. |
| 5,951,599 A | 9/1999 | McCrory |
| 5,980,514 A | 11/1999 | Kupiecki et al. |

(Continued)

FOREIGN PATENT DOCUMENTS

JP 2003250907 9/2003

*Primary Examiner* — Thomas J Sweet
*Assistant Examiner* — Brian Dukert
(74) *Attorney, Agent, or Firm* — G. Jo Hays; James Larson; James Pinkston

(57) ABSTRACT

A system for treating an aneurysm includes an expandable barrier positionable to bridge an aneurysm neck. The barrier may comprise a fiber mesh, a balloon or a molly anchor member, and may unroll, unfold, or inflate from a compact configuration to an expanded configuration. Expansion of the barrier may be greater radially than axially. A vaso-occlusive member comprising a coil or balloon may be deposited in the aneurysm. Another aneurysm treatment system comprises an outer fenestrated stent and/or an inner fenestrated sleeve, which may be implanted together adjacent an aneurysm neck to regulate blood flow to the aneurysm. The sleeve may be movable relative to the stent to open or occlude the fenestrations, which may vary in size, shape, and distribution. An intra-luminal vessel occlusion device comprises a stent and a sheath. A drawstring may be actuated to gradually close a sheath orifice to control blood flow through the vessel.

21 Claims, 18 Drawing Sheets

U.S. PATENT DOCUMENTS

| | | | |
|---|---|---|---|
| 5,984,944 A | 11/1999 | Forber | |
| 6,007,573 A | 12/1999 | Wallace | |
| 6,063,070 A | 5/2000 | Eder | |
| 6,063,104 A | 5/2000 | Villar et al. | |
| 6,063,111 A | 5/2000 | Hieshima | |
| 6,086,577 A | 7/2000 | Ken et al. | |
| 6,093,199 A | 7/2000 | Brown et al. | |
| 6,096,034 A | 8/2000 | Kupiecki et al. | |
| 6,139,564 A * | 10/2000 | Teoh | 606/213 |
| 6,143,015 A | 11/2000 | Nobles | |
| 6,159,197 A | 12/2000 | Heuser | |
| 6,168,592 B1 | 1/2001 | Kupiecki et al. | |
| 6,168,622 B1 | 1/2001 | Mazzocchi | |
| 6,171,326 B1 | 1/2001 | Ferrera et al. | |
| 6,193,708 B1 | 2/2001 | Ken et al. | |
| 6,231,597 B1 | 5/2001 | Deem et al. | |
| 6,263,236 B1 | 7/2001 | Kasinkas | |
| 6,287,318 B1 | 9/2001 | Villar | |
| 6,309,367 B1 | 10/2001 | Boock | |
| 6,312,421 B1 | 11/2001 | Boock | |
| 6,312,444 B1 | 11/2001 | Barbut | |
| 6,780,196 B2 | 8/2004 | Chin et al. | |
| 6,811,560 B2 * | 11/2004 | Jones et al. | 606/200 |
| 7,608,088 B2 * | 10/2009 | Jones et al. | 606/200 |
| 7,879,082 B2 | 2/2011 | Brown | |
| 2001/0036451 A1 * | 11/2001 | Goupil et al. | 424/78.38 |
| 2004/0044391 A1 * | 3/2004 | Porter | 623/1.1 |
| 2004/0098027 A1 * | 5/2004 | Teoh et al. | 606/200 |
| 2005/0119684 A1 | 6/2005 | Guterman et al. | |
| 2005/0267570 A1 | 12/2005 | Shadduck | |
| 2006/0095111 A1 | 5/2006 | Jones | |
| 2006/0206199 A1 * | 9/2006 | Churchwell et al. | 623/1.25 |
| 2007/0055362 A1 * | 3/2007 | Brown et al. | 623/1.35 |
| 2008/0221600 A1 * | 9/2008 | Dieck et al. | 606/157 |
| 2009/0069880 A1 | 3/2009 | Vonderwalde | |
| 2010/0161032 A1 | 6/2010 | Avellanet | |
| 2010/0161036 A1 | 6/2010 | Pintor | |
| 2011/0093002 A1 | 4/2011 | Rucker | |

* cited by examiner

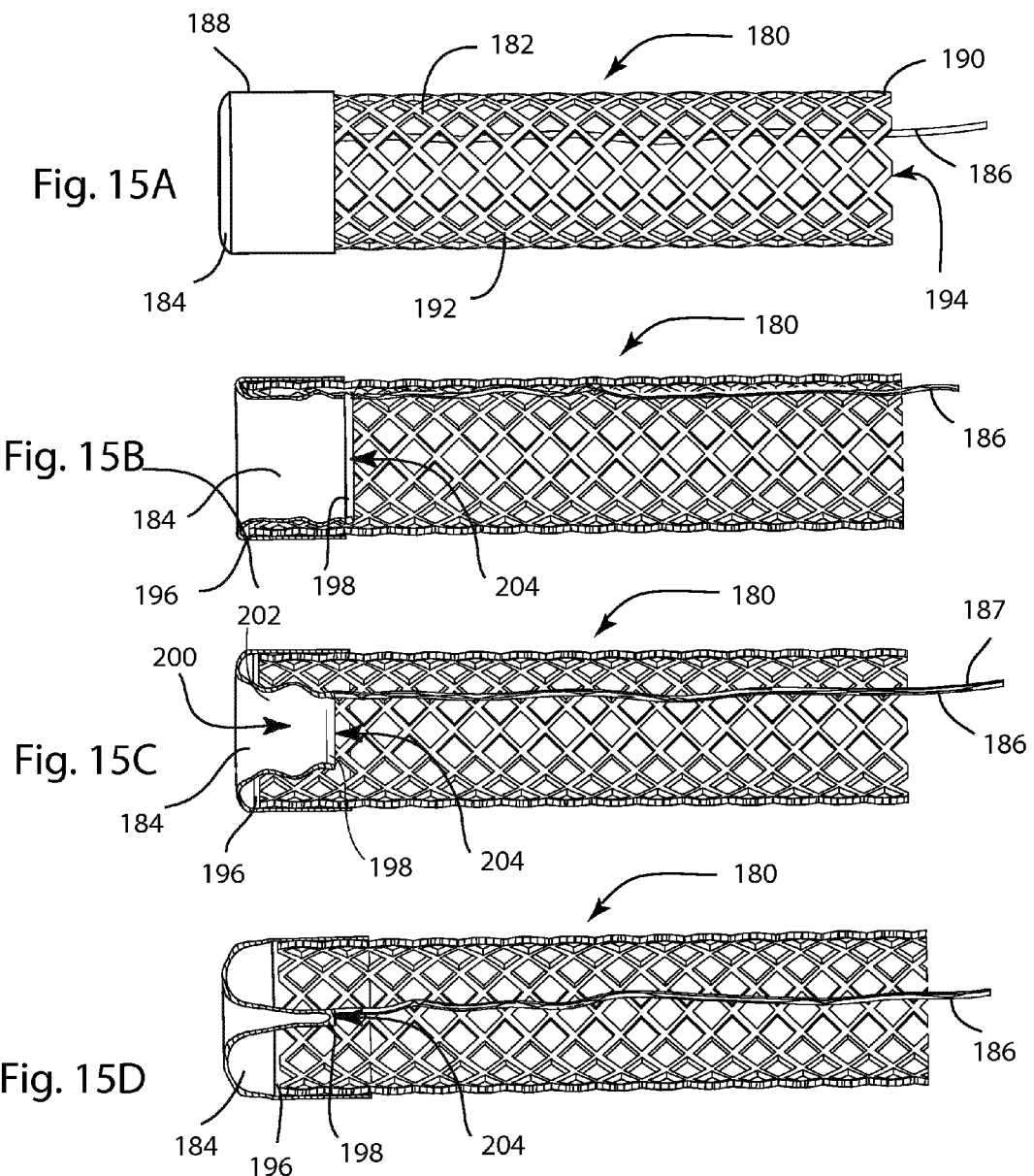

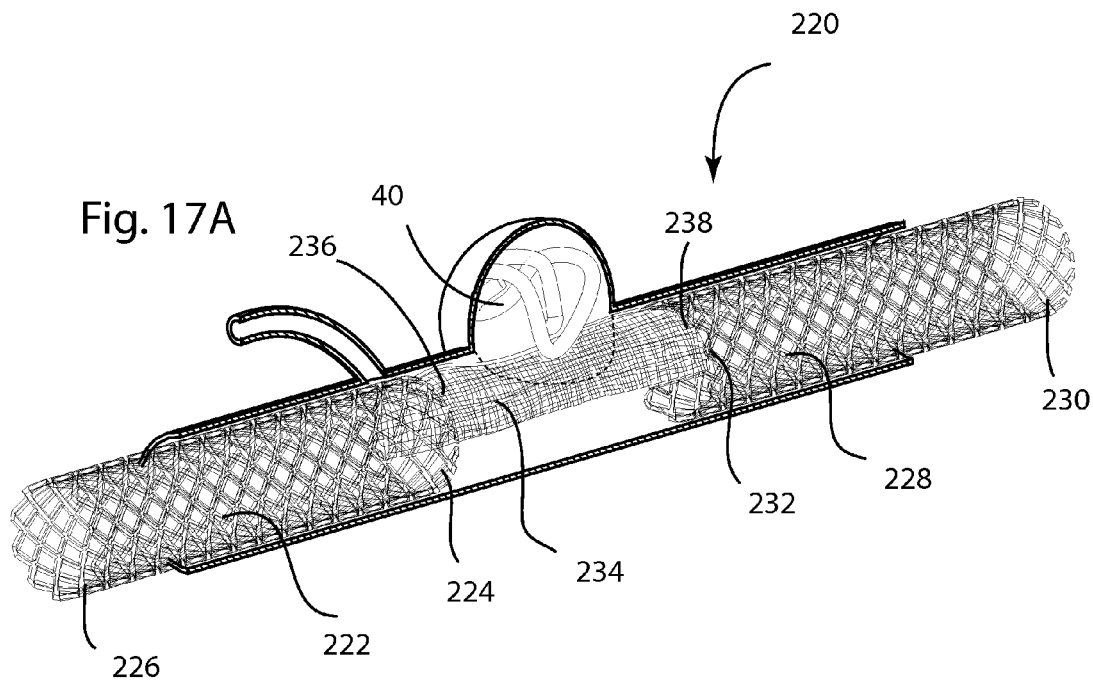
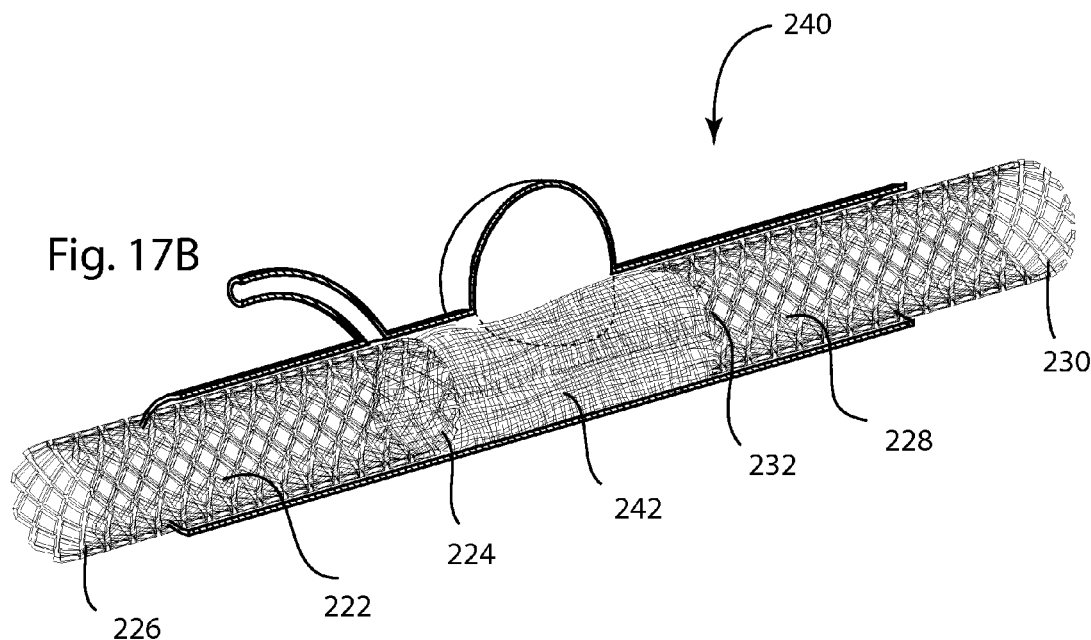

SYSTEMS AND METHODS FOR ANEURYSM TREATMENT AND VESSEL OCCLUSION

CROSS-REFERENCE TO RELATED APPLICATIONS

This application claims the benefit of:

U.S. Provisional Patent Application No. 61/106,670, filed Oct. 20, 2008, and is entitled DEVICES AND METHODS FOR ANEURYSM TREATMENT; and U.S. Provisional Patent Application No. 61/172,856, filed Apr. 27, 2009, and is entitled DEVICES AND METHODS FOR ANEURYSM TREATMENT.

The above-identified documents are incorporated herein by reference.

BACKGROUND OF THE INVENTION

1. The Field of the Invention

The invention relates to endovascular medicine, and more particularly, to systems and methods for aneurysm treatment and selective vessel occlusion.

2. The Relevant Technology

Cerebrovascular disease encompasses a broad spectrum of disorders, including intracranial aneurysms. Unruptured intracranial aneurysms have a prevalence of approximately 3.6 to 6% in the U.S. population and have an estimated annual rate of rupture between 10-28 per 100,000. Most individuals with aneurysms remain asymptomatic. Multiple risk factors for the development of intracranial aneurysms include: smoking, hypertension, positive family history and cocaine use. A number of inherited disorders have also been associated with the development of intracranial aneurysms. Ruptured intracranial aneurysms are the most common cause of non-traumatic subarachnoid hemorrhage (SAH). SAH secondary to aneurysm rupture is a potentially lethal event and carries a 50% morbidity-mortality rate.

An aneurysm is an abnormal localized dilation of a vessel. Aneurysms most frequently occur at sites of arterial bifurcation and are most commonly found in the brain. Pathologically, aneurysms have an absent or fragmented internal elastic membrane. Intracranial aneurysms are classified as saccular, fusiform, dissecting or false. Approximately 90% of intracranial aneurysms are saccular and are described by size, contour, orientation, location and neck size. Select unruptured and all ruptured intracranial aneurysms require either surgical or endovascular intervention.

Surgical intervention had long been the gold standard of care for the management of intracranial aneurysms and involves the placement of a clip across the aneurysm neck. A recent meta-analysis reviewing the risks of surgical repair found an overall mortality rate of 2.6 percent and a permanent morbidity rate of 10.9 percent. Endovascular treatment of intracranial aneurysms has developed over the last two decades. The procedure most commonly involves the insertion of a "coil" of wire into the aneurysm. The coil is delivered to the aneurysm through catheters, which are placed and guided through arteries. The Guglielmi Detachable Coil (GDC) pioneered the field of endovascular treatment of intracranial aneurysms and involved electrolytic detachable platinum coils that were placed directly into the fundus of the aneurysm via a microcatheter and detached from a stainless-steel micro-guidewire by an electrical current. Studies suggest that endovascular treatment may be associated with less procedural morbidity and mortality than conventional surgical techniques as well as reduced recovery time and earlier return to normal functioning.

Although endovascular techniques have created a paradigm shift in the management of intracranial aneurysms, the technique still has many limitations. This is particularly evident in the treatment of wide-necked, dissecting and fusiform aneurysms. Until recently, wide-necked aneurysms (defined as an aneurysm with a neck width>4 mm and/or a fundus/neck ratio<2) were not considered amenable to endovascular coiling for fear that a coil may prolapse into the parent vessel, leading to altered flow dynamics and stroke. More recently, expandable stents have been placed in the parent vessel—acting as a scaffold across the neck of the aneurysm, to prevent coil prolapse. For wide neck aneurysms, this has held promise in preventing coil migration. The introduction of the flexible intracranial stent (Neuroform; Boston Scientific) improved the management of these complex intracranial aneurysms, but was associated stent migration/misplacement and difficulties in coil delivery. In this system, the coils are inserted into the aneurysm dome via the fenestrations in the stent. The limitation with this design is that the fenestrations still allow blood to enter the aneurysm. Thus this strategy depends on the delivery of coils to occlude the dome. The introduction of the coils through the fenestrations in the stent can be associated with dislodgement/migration of the stent during the coiling. More recently, to avoid this problem, intracranial balloons have been used in conjunction with coils and stents. In this technique, the balloon is first inserted into the parent vessel, distal to the aneurysm. Once in place, the balloon is inflated, occluding distal blood flow. During this temporary occlusion, the coils are then inserted and are placed in the dome of the aneurysm. During this process, the balloon is intermittently inflated and deflated—in an attempt to prevent distal ischemia. Finally, once the coiling of the aneurysm is complete, a stent is placed across the neck of the aneurysm to prevent coil prolapse. The balloon is then deflated and distal blood flow resumed.

More recently, further advances have been made for the endovascular treatment of intracranial aneurysms using flow-diversion principles instead of space-occupying principles such as endovascular coiling. One of these devices, the JOSTENT (Abbott), is comprised of an expandable PTFE barrier between two stainless steel stents. Accordingly, it does not have fenestrations and has been used to extensively in cardiac endovascular procedures. This stent is placed in the parent vessel such that it directly occludes the neck of the aneurysm and prevents flow into the aneurysm. Unfortunately, this has had limited applications in the cranial vasculature, as its design is inflexible and difficult to position. In addition, its geometry poses a risk for occlusion of perforating vessels that may be in the vicinity of the aneurysm neck. Another flow-diversion device, the Pipeline Embolization Device (eV3), has been successful in decreasing blood flow into the aneurysm, while maintaining the patency of surrounding branch vessels. The Pipeline is a self-expanding cylindrical braided mesh construct that has decreased porosity size along the entire length of the stent which occludes the neck of the aneurysm. The cells of the mesh are sufficient to embolize the aneurysm while maintaining patency of the parent artery and minimizing disruption to flow into perforating vessels near the aneurysm.

The modern era of aneurysm treatment began with Hunterian ligation of the parent vessel. With increasing sophistication of surgical and endovascular management techniques, the indications for vessel occlusion for management of complex aneurysms are limited. A number of strategies have been devised for arterial occlusion including the Selverstone clamp, a device that allowed for gradual occlusion of the vessel. The rationale for gradual occlusion of the vessel was to promote the capacity for collateral circulation of the circle of Willis, in the hope of preventing post-occlusion cerebral infarction. This device could be reopened at the first sign of cerebral ischemia secondary to insufficient collateral circulation. A number of subsequent devices all incorporated an external mechanism that allowed the surgeon to gradually decrease the caliber of the vessel until ultimately achieving complete occlusion. In complex vascular disorders, deemed untreatable by both direct surgical or endovascular techniques, a test occlusion by balloon is performed by endovascular techniques. Unfortunately this does not provide a gradual occlusion of the vessel and does not allow for the gradual development of collateral circulation. At present, no endovascular technique allows for the gradual occlusion of a vessel.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 15A is a side view of a intra-luminal occlusion device comprising a stent, a sheath and a drawstring;

FIG. 15B is a cross-sectional side view of the intra-luminal occlusion device of FIG. 15A, with a sheath orifice in an open configuration;

FIG. 15C is a cross-sectional side view of the intra-luminal occlusion device of FIG. 15A, with a sheath orifice in an partially open configuration;

FIG. 15D is a cross-sectional side view of the intra-luminal occlusion device of FIG. 15A, with a sheath orifice in a closed configuration;

FIG. 17A is a partial cross-sectional view of an aneurysm with two stents in the vessel adjacent the aneurysm, and a half-pipe connection mesh bridging the aneurysm and connecting the two stents;

FIG. 17B is a partial cross-sectional view of an aneurysm with two stents in the vessel adjacent the aneurysm, and a cylindrical connection mesh bridging the aneurysm and connecting the two stents.

DETAILED DESCRIPTION OF THE PREFERRED EMBODIMENTS

Figure 1:
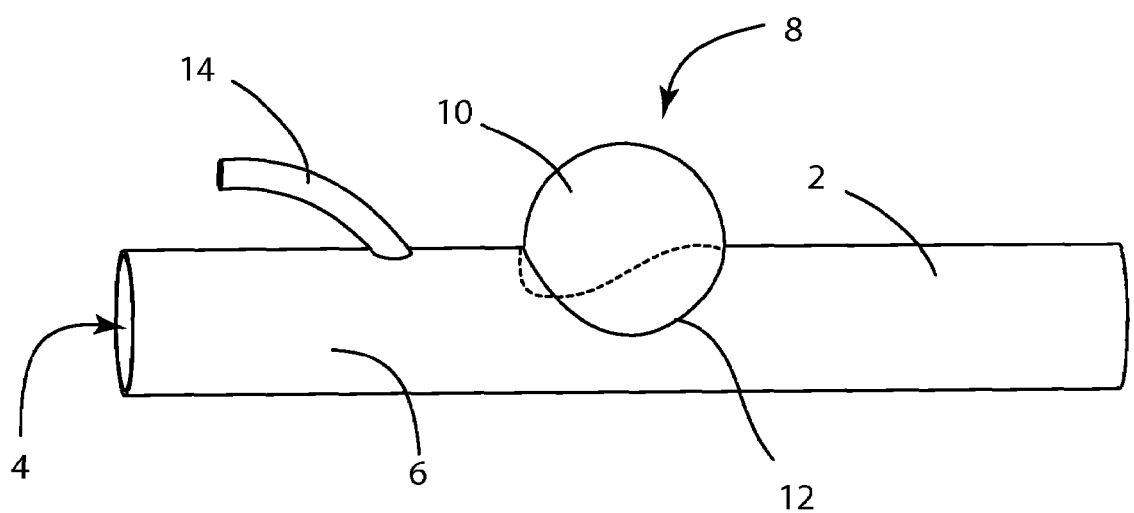
FIG. 1 is a stylized perspective side view of a representative wide-necked aneurysm of a parent blood vessel.

The present invention relates to systems and methods for providing aneurysm treatment, and selective vessel occlusion. Those of skill in the art will recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

Complex intracranial aneurysm treatment requires techniques for management of wide neck aneurysms, and for gradual occlusion of the parent vessel. Systems and methods disclosed herein provide a stent with an opening that could ultimately be open or closed, allowing the radiologist/surgeon to deploy coils or other various agents in a controlled and reliable manner. A number of these methods can incorporate an "open-closed window" technique. In at least one approach, the stent contains an opening, or aperture, that would allow the deployment of coils or other devices into the dome of the aneurysm ("open window"). Once occlusion of the aneurysm had been completed, the aperture would be closed—preventing dislodgement or prolapse of the coils ("closed window"). A mechanical means of controlling the aperture of a lumen within the body of a stent could be applied to all existing and future stents and could also be adapted to provide a means of gradual occlusion of a vessel.

In another approach, a stent comprises a plurality of apertures or cells, and an inner sleeve disposed within the stent similarly comprises a plurality of apertures or cells. By changing the juxtaposition of the sleeve relative to the stent by rotation and/or translation, allowing the stent cells to overlay the sleeve cells, the permeability of the stent can be varied.

Previously, wide neck aneurysms have been typically deemed "uncoilable" and instead required an open surgical approach. One approach disclosed herein utilizes a sleeve either inside or outside of the stent. The sleeve may have several wide openings in it as well as a closed (no openings) component. The sleeve may have a preconfigured curvature allowing it to bridge across the lumen of the vessel. To gain access to the aneurysm, the open segment of the sleeve may be positioned such that access to the neck of the aneurysm is provided. The opening in the sleeve may span across the lumen of the vessel, allowing for normal blood flow during the coiling of the aneurysm. The closed segment of sleeve may be positioned on the contralateral side of the vessel, thus leaving perforating vessels perfused. Once the coiling of the vessel is completed, the sleeve may then be retracted such that the "closed" segment is positioned at the neck of the aneurysm. By now closing access to the neck of the aneurysm, prolapse of coils or other agents may be prevented. This may also eliminate any further significant blood flow into the aneurysm. Alternatively, the closed segment of the sleeve may be positioned in such a manner as to occlude blood flow through the blood vessel during the coiling. Once coiling is complete, the sleeve could then be retracted to a "closed" position, occluding the opening (window) in the stent and preventing any further significant blood flow into the aneurysm.

Referring to FIG. 1, a stylized perspective view of a representative wide-necked aneurysm is shown. Parent vessel 2 defines a vessel lumen 4 having a substantially cylindrical lumen wall 6. An aneurysm 8 protrudes from the lumen wall 6, comprising an aneurysm sac 10 which joins the wall at an aneurysm neck 12. A branching vessel 14 branches from the parent vessel near the aneurysm.

Figure 2A:
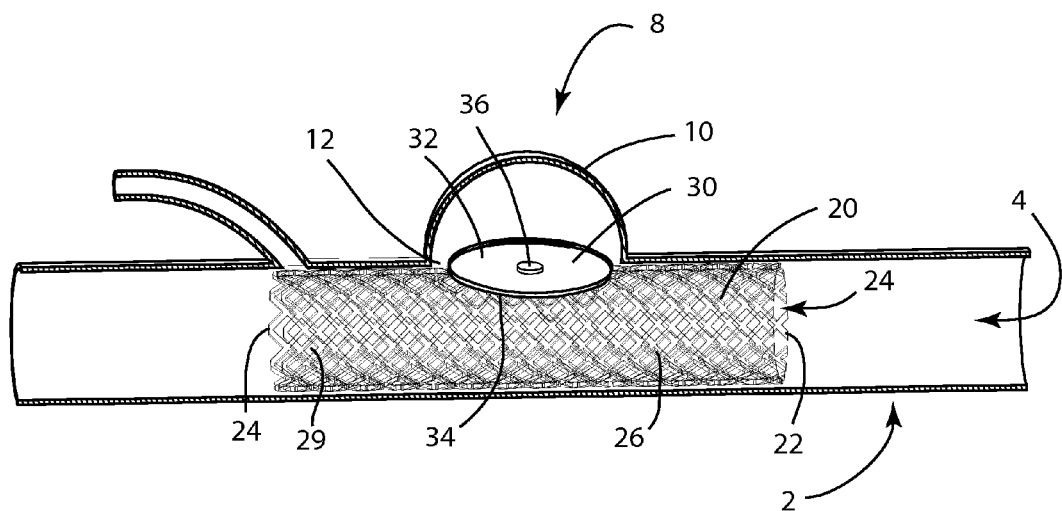
FIG. 2A is a partial cross-sectional side view of the aneurysm of FIG. 1 with a stent in the parent vessel and a barrier across the aneurysm neck.

Referring to FIG. 2A, a cutaway view of parent vessel 2 and aneurysm 8 is shown, with a stent 20 in the vessel lumen 4 and a barrier 30 implanted to extend across the aneurysm neck 12, forming an aneurysm treatment system. The stent 20 may be a fenestrated stent known in the art, and comprises a first end 22, a second end 24, and a stent wall 26 which defines a stent lumen 28. The stent wall comprises plurality of fenestrations, or cells 29, allowing flexibility of the stent, and allowing blood flow through the stent wall. The stent may be made to have anti-thrombogenic properties on the inner surface and thrombogenic properties on the exterior surface. Barrier 30 includes a first, or outer side 32 which may be also be coated or treated with a thrombogenic treatment, and a second, or inner side 34 which may be coated or treated with an anti-thrombogenic treatment. In some embodiments, an opening 36 may communicate with the first and second sides 32, 34. The opening 36 may engage with an instrument for implantation, deployment and/or expansion of the barrier.

The barrier 30 may serve as a shield or blanket to slow or prevent blood flow into the aneurysm, providing an environment for spontaneous thrombosis of the aneurysm and/or provide support at the aneurysm neck to prevent prolapse of coils or other intra-saccular aneurysm implants into the parent vessel. Barrier 30 may be delivered before, in tandem with, or after placement of the stent. The barrier 30 may be rolled, coiled up, folded, deflated, compressed, or otherwise retracted to form a compact configuration, and it may be deployed or expanded to form an expanded configuration. The barrier may be delivered to the aneurysm through the stent wall 26 in the compact configuration, then unrolled, uncoiled, unfolded, inflated, uncompressed or otherwise expanded to form the expanded configuration like that seen in FIG. 2A. The barrier may extend substantially across the aneurysm neck, in which the barrier blocks the opening between the aneurysm and the vessel to minimize or entirely prevent bloodflow between the aneurysm and the vessel, yet does not touch the neck, in order to prevent rupture of the aneurysm. The barrier may also be delivered alongside the stent, passing between the stent wall 26 and the vessel lumen wall. A microcatheter may deliver the barrier to the aneurysm before delivery of the stent, or through or alongside the stent after delivery of the stent. In some embodiments, the barrier is formed as a patch on a portion of the stent wall 26.

Figure 2B:
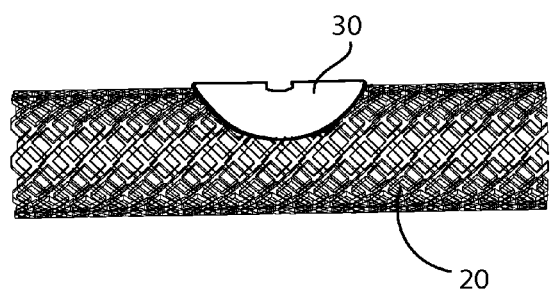
FIG. 2B is a side view of the stent and barrier of FIG. 2A with the barrier in a curved configuration.

FIG. 2B depicts the barrier 30 and the stent 20, with the barrier in a curved configuration. This configuration may allow the barrier to more completely shield the aneurysm neck to prevent blood flow from the vessel into the aneurysm.

Figure 3A:
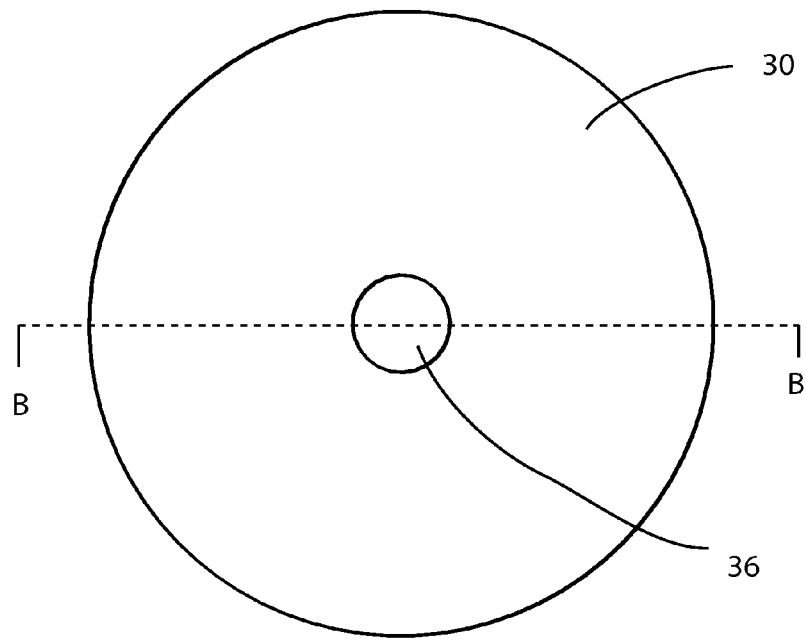
FIG. 3A is a top view of the barrier of FIG. 2A.
Figure 3B:
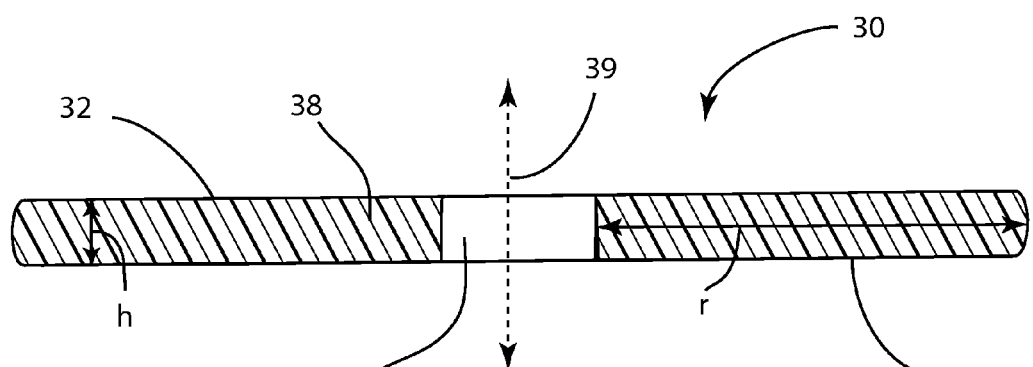
FIG. 3B is a cross-sectional side view of the barrier of FIG. 3A, taken along line B-B.

FIG. 3A depicts a top view of barrier 30, and FIG. 3B is an enlarged cross-sectional lateral view taken along section line B. Barrier 30 may be a single, solid member, or may have an interior space 38 formed between the first and second sides 32, 34. When the barrier is expanded or inflated, a volume of the interior space may increase; when the barrier is retracted or deflated, the volume may decrease. The barrier may expand or contract laterally, increasing or decreasing in radius r relative to a longitudinal axis 39, which may also be referred to as radial expansion. It may also expand or contract axially, increasing or decreasing in height h. In some embodiments, radial expansion of the barrier may be greater than axial expansion. Barrier 30 may be comprised of materials including nylon, polypropylene, polyester, polyurethane, polyvinyl chloride, Teflon, ePTFE, PTFE, polyethylene, polypropylene, silicone, PEEK, and/or hydrogel, among others. These materials may take the form of a fabric, or fiber mesh in which the fibers are woven, knitted, coiled, braided or otherwise intermeshed together. A mesh barrier may have an interior space formed between the outer strands of the mesh. In an alternative embodiment, the barrier may comprise beads, in which each individual bead is larger in diameter than the maximum width of a stent cell 29, preventing passage of the beads through the stent cells. Such beads may comprise hydrogel, and swell to enlarge when deposited in the aneurysm sac and exposed to fluid. The barrier may be symmetrical axially and radially as shown in FIGS. 3A and 3B, or it may be asymmetrical in any direction.

Figure 4:
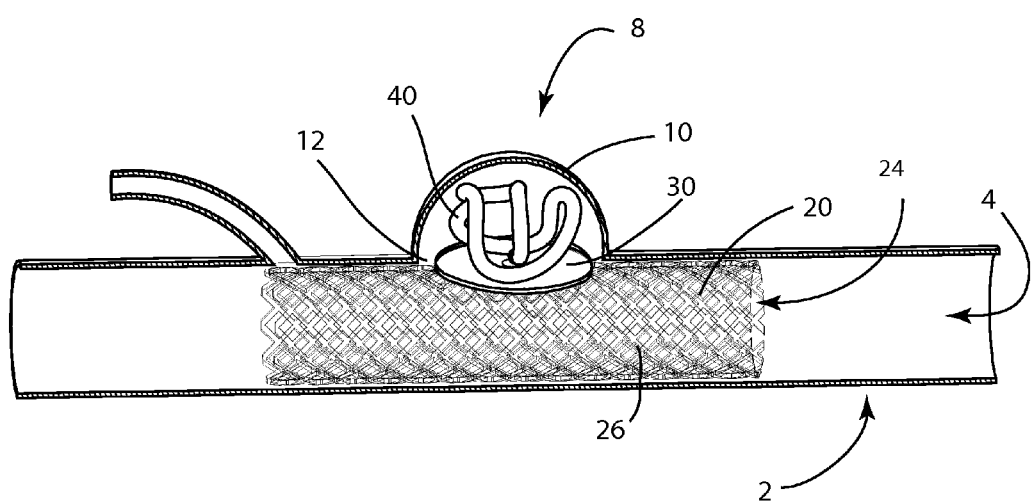
FIG. 4 is a partial cross-sectional side view of the aneurysm, stent and barrier of FIG. 2A and a vaso-occlusive coil in the aneurysm.

An intra-saccular vaso-occlusive member may be included in the aneurysm treatment system. Referring to FIG. 4, a vaso-occlusive member comprising a coil 40 is shown implanted in the aneurysm sac; the barrier 30 prevents the coil 40 from penetrating the stent 20 and/or escaping the aneurysm through the aneurysm neck 12. The coil 40 may comprise one or a plurality of coil members, and may be a coil known in the art. Implantation of the coil may occur prior to, with, or after implantation of the barrier. A coil introduction instrument comprising a microcatheter carrying the coil may be advanced through the stent lumen 24, through the stent wall 26 and through the barrier opening 36, and the coil deposited from the microcatheter into the aneurysm sac 10. Alternatively, the microcatheter may be advanced alongside the stent and through the aneurysm neck 12, and the coil deposited into the aneurysm sac. The coil introduction instrument may further comprise a shield located proximal to the microcatheter tip, the shield positionable to bridge the aneurysm neck as the coil is introduced into the aneurysm, preventing migration of the coil out of the aneurysm sac.

In some embodiments, a vaso-occlusive member may comprise a gel and/or foam scaffold which is injected into the aneurysm under low pressure, after placement of a barrier in the aneurysm neck. A microcatheter tip is inserted through an opening such as barrier opening 36, and the gel or foam is injected into the aneurysm sac. Following insertion, the material may solidify and bind together.

In another embodiment, the vaso-occlusive member may comprise a soft textile coil impregnated with a clotting agent. This type of coil may be implanted through the wall of a stent, but without a barrier. After implantation of the coil, blood is allowed to flow into the aneurysm through the stent, and the clotting agent on the coil is activated by the blood to bind the coil to itself, using blood as the binding agent.

Figure 5A:
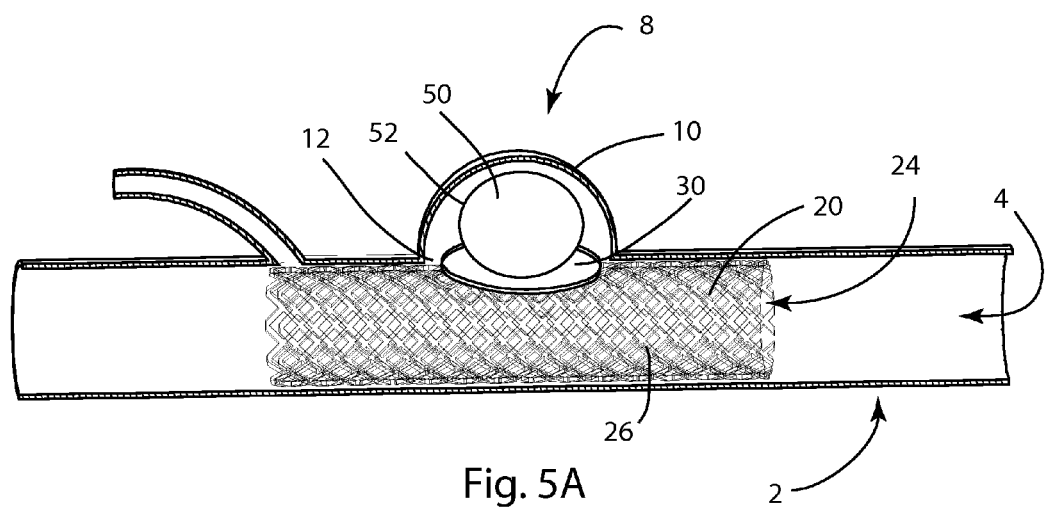
FIG. 5A is a partial cross-sectional side view of the aneurysm, stent and barrier of FIG. 2A and a vaso-occlusive elliptical balloon in the aneurysm.
Figure 5B:
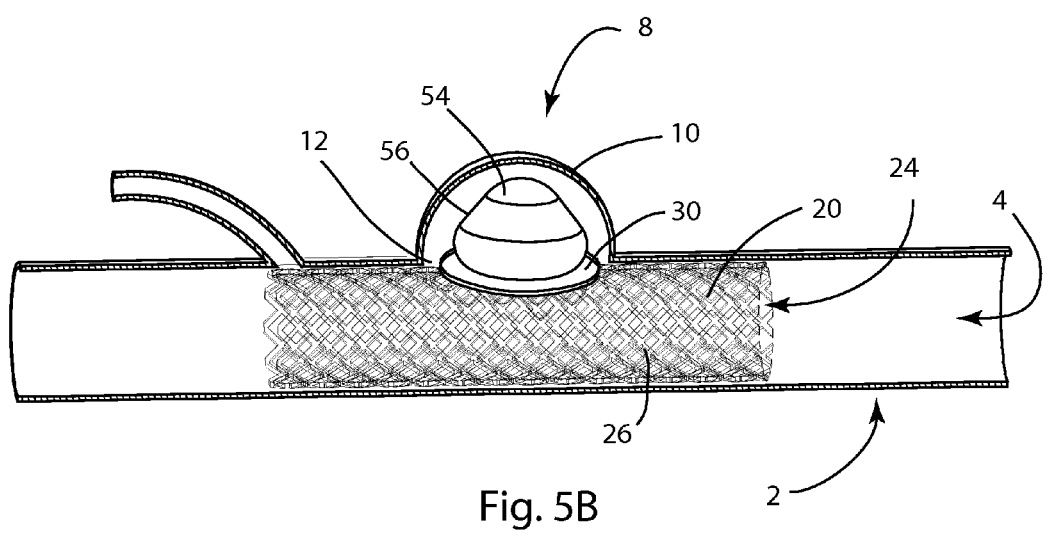
FIG. 5B is a partial cross-sectional side view of the aneurysm, stent and barrier of FIG. 2A and a vaso-occlusive conical balloon in the aneurysm.

Referring to FIGS. 5A and 5B, a vaso-occlusive member comprising a balloon may be implanted in the aneurysm. A vaso-occlusive balloon may comprise an elastomeric sheath comprising silicone, polyurethane, or hydrogel, among other material. The balloon may comprise an elliptical shape as depicted, a round shape, a conical shape, or a ring or donut shape with a central opening, among others. FIG. 5A depicts a round balloon 50 comprising an elastomeric sheath 52, while 5B depicts a nosecone balloon 54 comprising an elastomeric sheath 54 with a plurality of zones. A nipple or other port may be included for balloon inflation and/or deflation. The elastomeric sheath may comprise a compliant material with a uniform level of compliance or elasticity. In other embodiments, the elastomeric sheath may comprise zones with varying levels of compliance or elasticity, such that the balloon inflates to a greater extent in some zones than in others. For example, the balloon may inflate to a greater extent radially than axially, in order to more effectively obscure the neck of the aneurysm. The balloon may also be pre-shaped to inflate to a specific predetermined shape, such as those previously listed.

It is appreciated that the vaso-occlusive balloon may be implanted with or without a barrier such as barrier 30, and it may be implanted before, with, or after the barrier. The balloon may be implanted using the methods disclosed previously for implantation of a coil. A microcatheter may be actuated to implant the balloon into the aneurysm through or alongside the stent, and a microcatheter may also deliver fluid into the balloon to inflate the balloon. The barrier opening 36 may allow passage of the microcatheter to the balloon. Suitable fluids for inflation may include air, saline solution, hydrogel, silicone, polyvinyl acetate (PVA), and curable adhesives, among others.

Figure 6A:
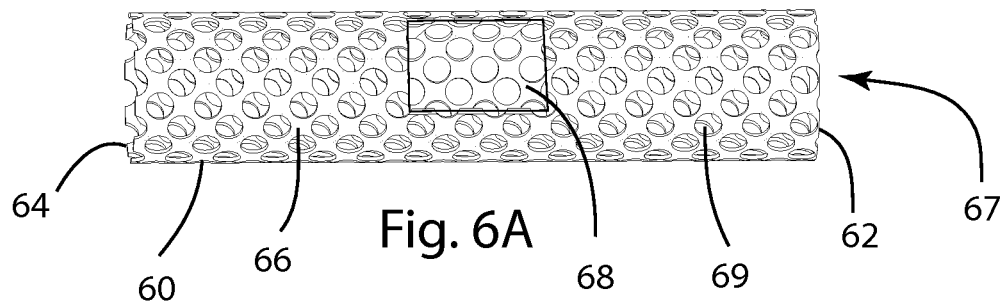
FIG. 6A is a top view of a sleeve with a cutout window.
Figure 6B:
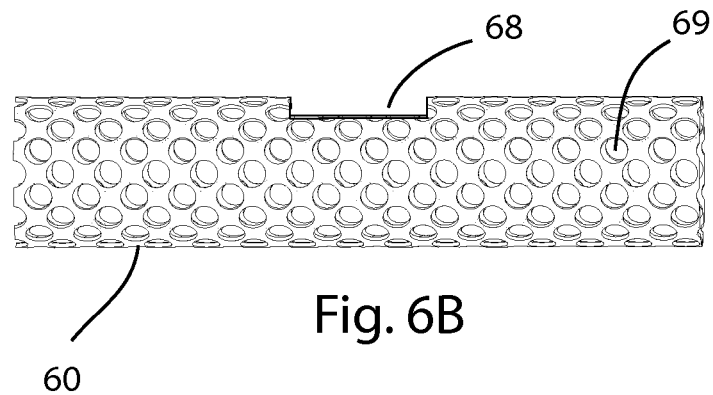
FIG. 6B is a side view of the sleeve of FIG. 6A.
Figure 6C:
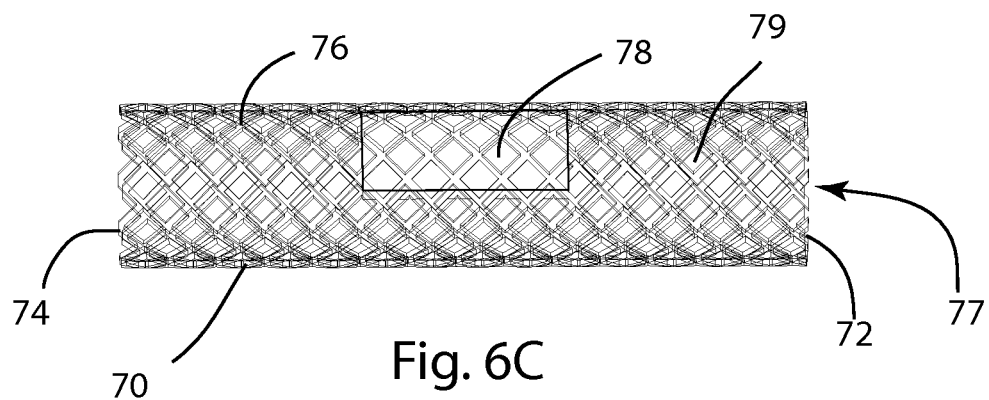
FIG. 6C is a top view of a stent with a cutout window.

Another approach to occluding an aneurysm comprises a first stent, and a second stent or sleeve which may be deployed inside or outside the stent. The stent and sleeve may be rotated and/or axially translated relative to one another to provide an open or closed window to the aneurysm, and to provide varying degrees of blood flow through the stent and sleeve walls. FIGS. 6A and 6B depict a sleeve 60 comprising a first end 62, a second end 64, and a stent wall 66 which defines a sleeve lumen 67. The sleeve wall comprises plurality of fenestrations, or sleeve cells 69, allowing flexibility of the sleeve, and allowing blood flow through the sleeve wall. A sleeve window 68 is located in the sleeve wall. Depicted in FIG. 6C, stent 70 comprises a first end 72, a second end 74, and a stent wall 76 which defines a stent lumen 77. The stent wall comprises plurality of fenestrations, or stent cells 79, allowing flexibility of the stent, and allowing blood flow through the stent wall. A stent window 78 is located in the stent wall. As seen in FIGS. 6A-6C, window 68 may be smaller than window 78; in other embodiments, window 68 may be larger than window 78, or they may be the same size. When sleeve 60 is disposed within stent 70, sleeve 60 and/or stent 70 may be rotated and/or translated relative to one another to allow windows 68, 78 to line up to allow passage of blood, vaso-occlusive members or other bodies through the windows. Similarly, the sleeve cells 69 and stent cells 79 may be partially or fully lined up to allow maximal blood flow through the sleeve and stent walls 66, 76, or partially or completely occlude blood flow through the sleeve and stent walls. Sleeve 60 may also be disposed outside of stent 70. The sleeve and stent windows 68, 78 may be rectangular as depicted in FIGS. 6A-6C, or they may be round, oval, or any other shape.

Figure 7A:
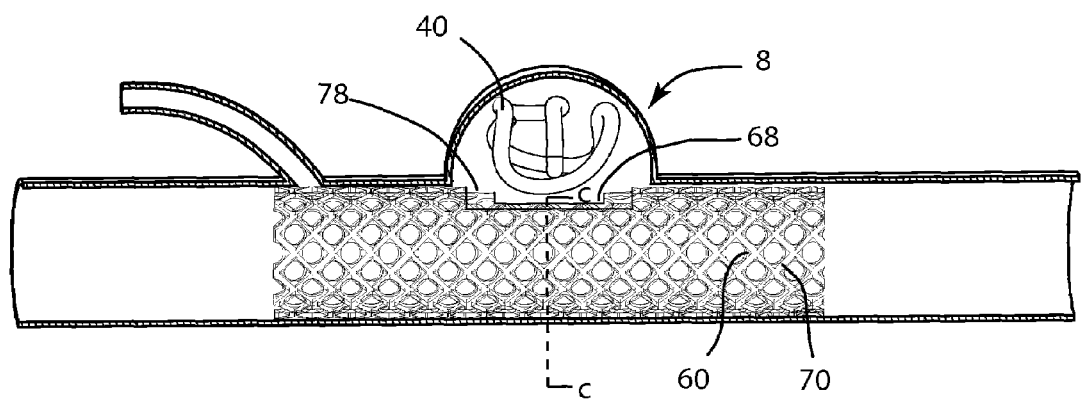
FIG. 7A is a partial cross-sectional view of an aneurysm with the sleeve of FIG. 6A inside the stent of FIG. 6C, the sleeve and stent juxtaposed to provide an open window and open stent cells, and a vaso-occlusive coil.
Figure 7B:
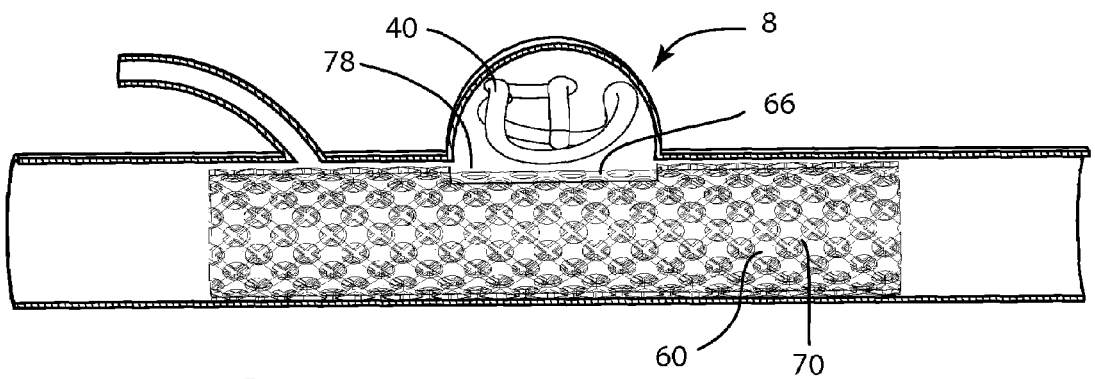
FIG. 7B is a partial cross-sectional view of the aneurysm, sleeve, stent and coil of FIG. 7A, with the sleeve rotated relative to the coil to provide a closed window and occluded stent cells.
Figure 7C:
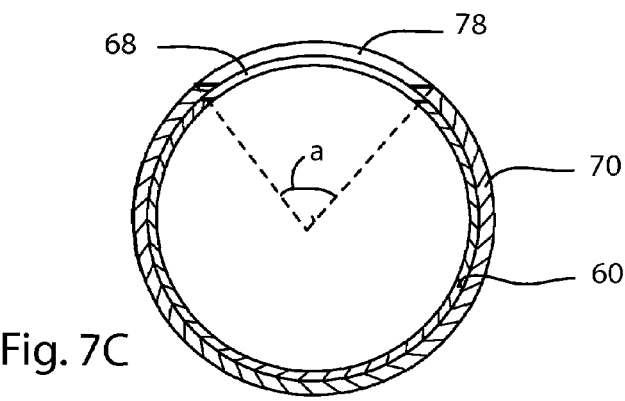
FIG. 7C is a cross-sectional view of the sleeve and stent of FIG. 7A taken at line C-C, showing an angle of the open window.

FIGS. 7A and 7B depict stent 70 and sleeve 60 placed in a vessel adjacent aneurysm 8. In FIG. 7A, sleeve 60 and stent 70 are juxtaposed so that window 68 and 78 are lined up, creating an unimpeded opening between the aneurysm 8 and the lumen of the sleeve. Coil 40, or other intra-saccular materials as desired, may be implanted in the aneurysm when the sleeve and stent are in this "open" configuration. FIG. 7B depicts sleeve 60 and stent 70 in a "closed" configuration, in which sleeve 60 has been rotated so that sleeve window 68 is no longer lined up with stent window 78. In the "closed" position, coil 40 cannot pass out through the windows, and blood flow may be impeded. FIG. 7C is an end cross-sectional view of the sleeve and stent in the "open" configuration of FIG. 7A.

The window dimensions may vary in length and width. Preferably, the window widths may range from 10° to 180° of the circumference of the respective sleeve or stent. More preferably, the window width ranges from 30° to 60° of the circumference of the respective sleeve or stent. In an exemplary embodiment, the window width is 45° of the circumference of the respective sleeve or stent. In the embodiment depicted in FIG. 7C, both stent 70 and sleeve 60 have a window width which is subtended by angle α of approximately 40°.

In another embodiment of the invention, blood flow to an aneurysm may be decreased or entirely occluded by a device comprising an outer stent and an inner stent or sleeve, placed in the vessel adjacent the aneurysm. The outer stent may have fenestrations or cells of regular size and distribution, while the inner sleeve may have fenestrations or cells of differing sizes which may be distributed regularly or within zones. When the inner sleeve is disposed in the outer stent and rotated and/or translated relative to the outer sleeve, the overlay of the outer stent relative to the inner sleeve can increase or decrease effective outer stent cell sizes to change the permeability of the stent wall to blood flow. Changing the effective outer stent cell size may increase, decrease or occlude flow to the aneurysm.

Figure 8A:
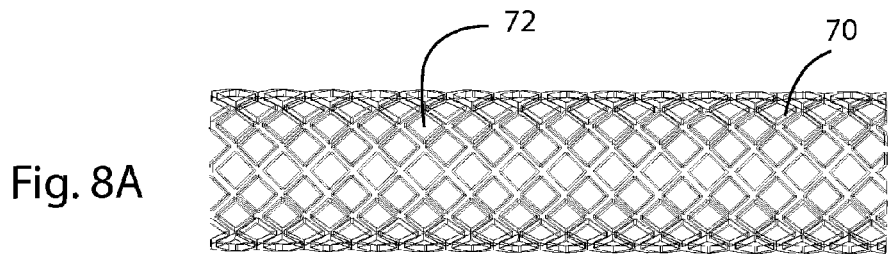
FIG. 8A is a side view of a stent with fenestrations.
Figure 8B:
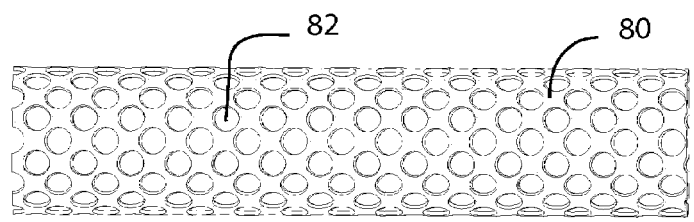
FIG. 8B is a side view of a sleeve with fenestrations.

Referring to FIGS. 8A through 8F, several embodiments of outer stent and inner sleeve configurations are shown. FIG. 8A depicts flexible stent 70, comprising quadrilateral fenestrations 72. FIG. 8B depicts sleeve 80, comprising substantially round fenestrations 82. When sleeve 80 is disposed in stent 70, the sleeve fenestrations 82 may line up with the stent fenestrations 72 similar to FIG. 7A, in which each sleeve fenestration is lined up with a stent fenestration to create relatively unimpeded openings. Sleeve 80 may be rotated relative to stent 70 so that the fenestrations no longer line up in an open fashion, similar to FIG. 7B. In this configuration, blood flow would be impeded in comparison to the configuration in FIG. 7A.

Figure 8C:
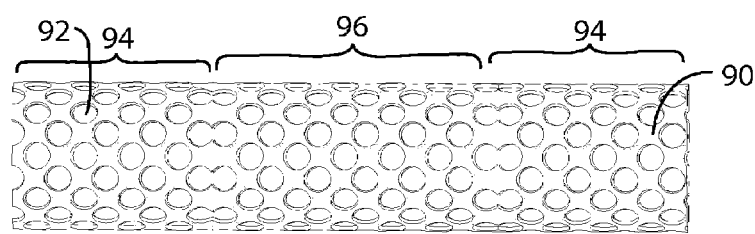
FIG. 8C is a side view of a sleeve with fenestration zones.

FIG. 8C depicts sleeve 90, which has sleeve fenestrations 92 distributed in three zones. Two first zones 94 have fenestrations distributed in circumferential rows, while in second zone 96, the rows of fenestrations are offset from those in zones 94. Zones 94 and 96 are circumferential; however it is appreciated that in other embodiments the zones could be arranged longitudinally along the length of the sleeve.

Figure 8D:
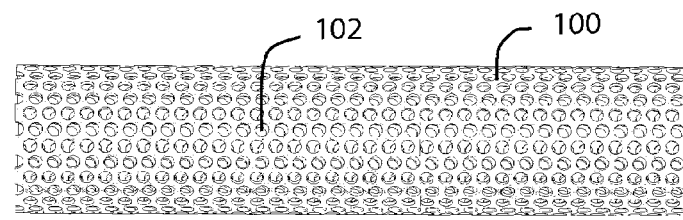
FIG. 8D is a side view of a sleeve with fine fenestrations.

FIG. 8D depicts sleeve 100 having fenestrations 102. Sleeve fenestrations 102 are relatively smaller than those in the other sleeve embodiments. When sleeve 100 disposed in stent 70, together they may create a device with relatively less blood flow permeability than that of the other embodiments depicted.

Figure 8E:
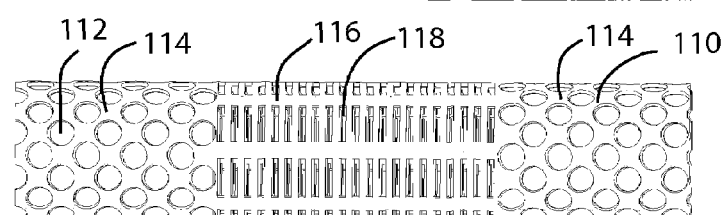
FIG. 8E is a side view of a sleeve with two zones of round fenestrations and one zone of vent-like fenestrations.

FIG. 8E depicts a sleeve 110 having first zones 114 comprising round fenestrations 112, and second zone 116 has slot-like or vertical vents 118. Each vent comprises a flap which may be open when there is no blood or fluid flow through the lumen of the sleeve, and closed by fluid pressure when blood flows through the lumen.

Figure 8F:
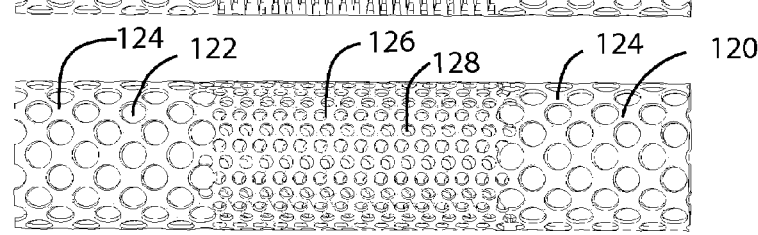
FIG. 8F is a side view of a sleeve with two zones of round fenestrations and one zone of finer round fenestrations.

FIG. 8F depicts a sleeve 120 having two zones 124 with large fenestrations 122, while zone 126 has relatively finer fenestrations 128.

Any of the sleeves disclosed in FIGS. 8B-8F may be combined with stent 70 or another stent to form aneurysm treatment devices with varying permeability to fluids. As described, the sleeve and/or stent may be rotated and/or translated relative to one another to create open, partially open, or closed cells. Additionally, a stent may comprise any of the cell or fenestration configurations and distributions disclosed herein. Other methods of affecting cell size or opening can include fluid pressure, or using radio frequency (RF) or ultrasonic energy to change cell sizes in specifically zoned portions of a stent and/or sleeve in situ. For example, an ultrasonic energy delivery device may comprise a guidewire through which ultrasound is passed. In another embodiment, a stent and sleeve combination may have an integrally formed zone of compliance that is activated by axially stretching or compressing the stent and sleeve. In other embodiments, the stent and sleeve may be coupled or fused together during manufacture. The stents and sleeves disclosed herein may be implanted with or without a vaso-occlusive member such as a coil or balloon, and with or without a barrier member.

Figure 9A:
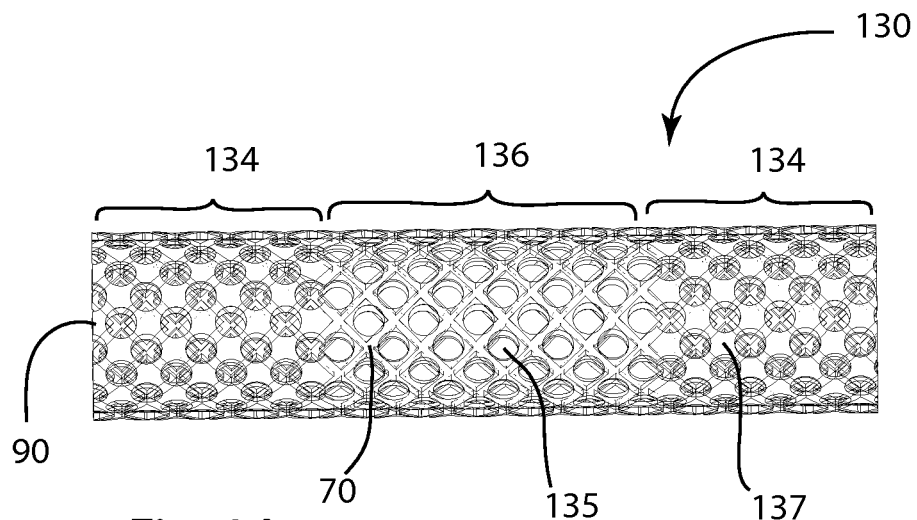
FIG. 9A is a side view of the sleeve of FIG. 8C inside the stent of FIG. 8A, the sleeve and stent juxtaposed to provide open stent cells in a central zone and occluded stent cells in two flanking zones.
Figure 9B:
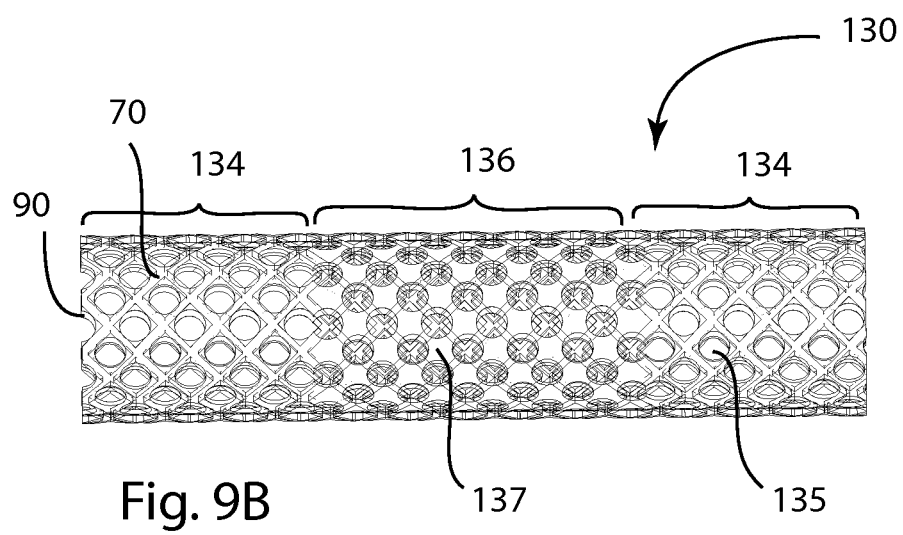
FIG. 9B is a side view of the sleeve and stent of FIG. 9A, the sleeve and stent juxtaposed to provide occluded stent cells in the central zone and occluded stent cells in the two flanking zones.

Referring to FIGS. 9A and 9B, occlusion device 130 comprises outer stent 70 and inner sleeve 90. Three zones are distributed circumferentially about the device; two zones 134 adjacent first and second ends of the device, and zone 136 substantially centrally located. The occlusion device 130 comprises an open configuration as seen in FIG. 9A, in which the sleeve 90 and stent 70 are juxtaposed to form open fenestrations 135 in the central zone 136. End zones 134 comprise closed fenestrations 137. In FIG. 9B the sleeve 90 has been rotated relative to the stent 70 to create a closed configuration, in which central zone comprises closed fenestrations 137. When implanted in a vessel so that an aneurysm is adjacent central zone 136, blood flow to the aneurysm may be allowed when the device is in the open configuration depicted in FIG. 9A, and blood flow may be occluded when the device is in the closed configuration depicted in FIG. 9B. Of course, the sleeve 90 may be partially rotated relative to the stent 70 to cause partial occlusion. Also, if desired, a coil 40 or other vaso-occlusive member may be implanted in the aneurysm sac before or after placement of occlusion device 130.

Figure 10A:
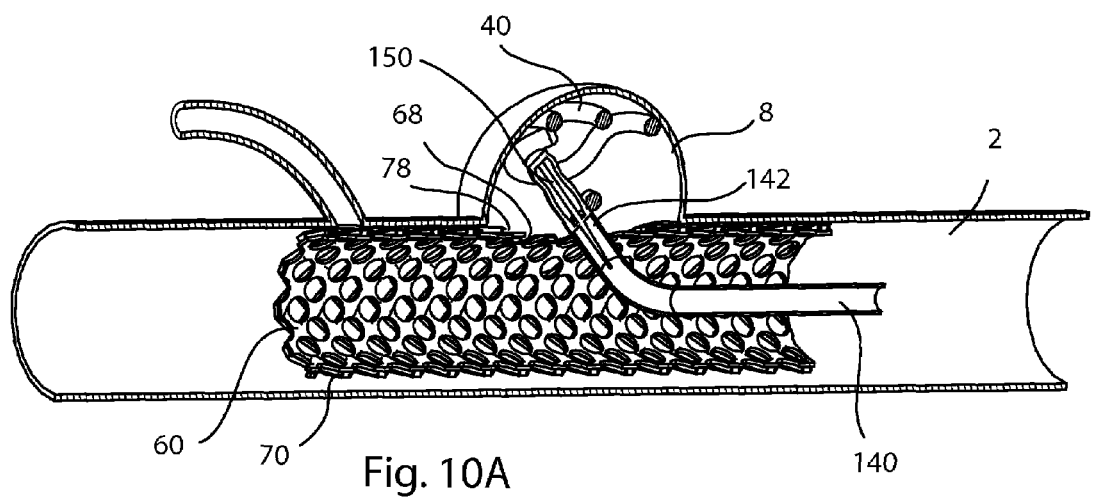
FIG. 10A is a partial cross-sectional view of the aneurysm, coil, sleeve and stent with cutout windows of FIG. 7A, and a microcatheter depositing an expandable molly anchor barrier into the aneurysm.
Figure 10B:
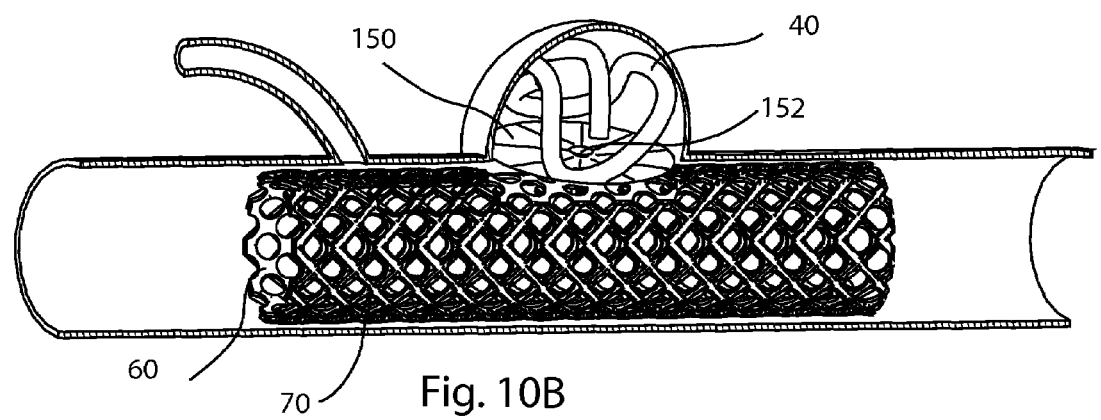
FIG. 10B is a partial cross-sectional view of the aneurysm, coil, sleeve, stent and molly anchor barrier of FIG. 10A, with the barrier expanded across the neck of the aneurysm.
Figure 10C:
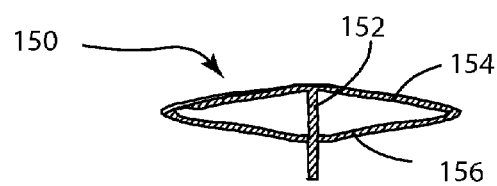
FIG. 10C is a cross-sectional view of the molly anchor barrier of FIG. 10B.

An aneurysm treatment comprising a barrier and a vaso-occlusive device may be implanted in conjunction with an outer stent and inner sleeve device such as those disclosed in FIGS. 6-9. Referring to FIG. 10A, a longitudinal cross-section of a vessel 2 with an aneurysm 8 is shown. Outer stent 70 and inner sleeve 60 have been introduced into the vessel and juxtaposed so that windows 68, 78 are aligned to create an opening into the aneurysm. A microcatheter 142 is inserted into the inner sleeve lumen and a microcatheter tip 142 protrudes through the open windows 68, 78. A coil 40 has been introduced into the aneurysm, and an expandable barrier 150 comprising a molly anchor is projecting out of the microcatheter tip. In FIG. 10B, the expandable barrier 150 has been deposited into the aneurysm neck and is expanded. Inner sleeve 60 has been translated relative to outer stent 70 to close the opening into the aneurysm. In FIG. 10C, a cross-sectional view of the expandable barrier 150 shows a central stem 152, an upper or outer side 154, and a lower or inner side 156. Outer side 154 is coupled to stem 152 and stem 152 is slidable relative to inner side 156. Thus, expandable barrier 150 can collapse and deploy like an umbrella. In FIG. 10A, expandable barrier 150 is in a retracted or compact configuration, and in an expanded configuration in FIG. 10B. In some embodiments, coil 40 may be coupled to expandable barrier 150 to be deployed with the barrier; or they may be implanted separately. In another embodiment, the molly anchor barrier may be implanted without a coil.

The molly anchor type barrier may comprise wire including Nitinol, wire mesh, an elastomeric sheath, fabric, or other materials previously listed. In addition, the molly anchor barrier may comprise hydrogel, so that it enlarges in size once implanted and exposed to fluid. In other embodiments, a coil may be formed integrally with, or connected to, a mesh or fabric skirt. Following insertion of the coil into the aneurysm, the attached skirt is deposited into the aneurysm neck and unrolls or unfolds to form a barrier to occlude the aneurysm neck, and prevent escape or migration of the coil into the vessel.

Figure 11:
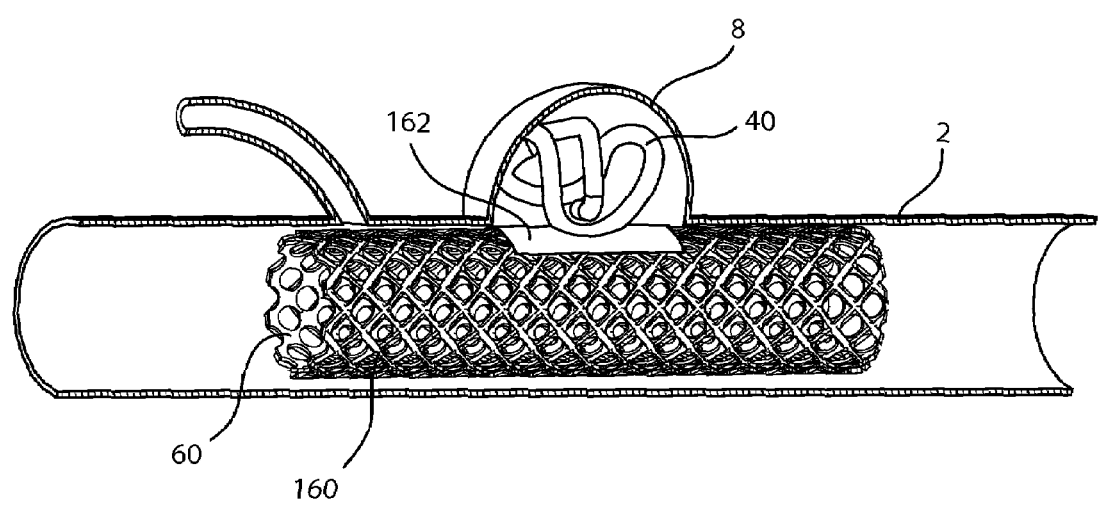
FIG. 11 is a partial cross-sectional view of an aneurysm with a coil in the aneurysm and a sleeve inside a stent in the vessel adjacent the aneurysm, the stent having a barrier formed on the stent.

Referring to FIG. 11, an alternative embodiment of an occlusion device comprises an inner sleeve, a coil, and a barrier formed on an outer stent and implanted into a vessel to occlude blood flow into an aneurysm. Stent 160 comprises a flexible, expandable stent with a barrier patch 162 formed on a portion of the stent wall. Stent 160 may be placed in the vessel with inner sleeve 60 positioned in the stent lumen. The sleeve 60 and stent 160 may be juxtaposed relative to one another so that the patch 162 is not occluding the aneurysm neck, and coil 40 is deposited by a microcatheter through the open cells of sleeve 60 and stent 160. After deposition of the coil into the aneurysm, stent 160 may be rotated relative to the coil until the patch 162 covers the aneurysm neck. Alternatively, the coil may be inserted along the outer surface of the stent; or, the stent may be installed after deposition of the coil in the aneurysm sac. The patch 162 may be entirely occlusive to blood flow, or have a greater degree of permeability. The patch 162 may comprise materials including nylon, polypropylene, polyester, polyurethane, polyvinyl chloride, Teflon, ePTFE, PTFE, polyethylene, polypropylene, silicone, PEEK, and/or hydrogel, among others. The patch may be made to have anti-thrombogenic properties on the inner surface and thrombogenic properties on the exterior surface. In an alternative embodiment, stent 160 having a barrier patch 162, and a coil or other intra-saccular device may be deployed without inner sleeve 60.

Figure 12A:
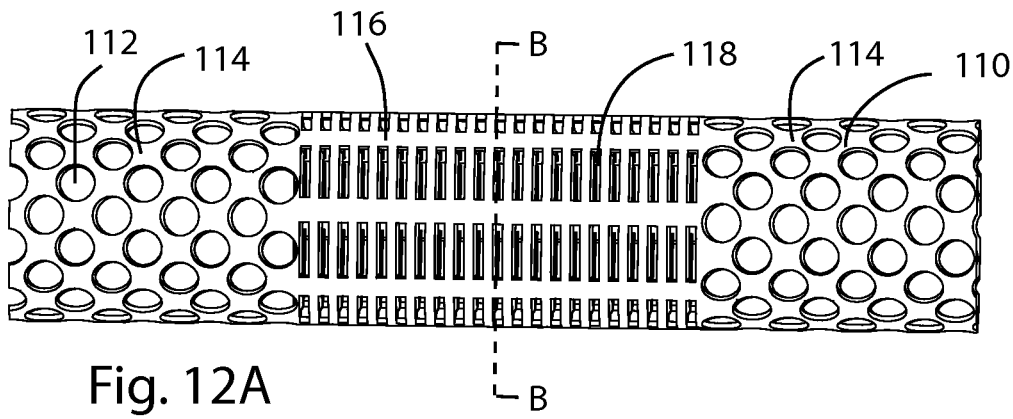
FIG. 12A is a side view of the sleeve of FIG. 8E.
Figure 12B:
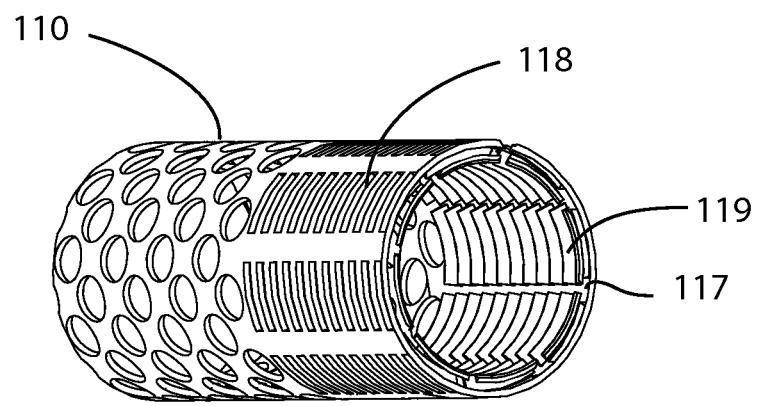
FIG. 12B is a perspective cross-sectional view of the sleeve of FIG. 12A, taken at line B-B.
Figure 12C:
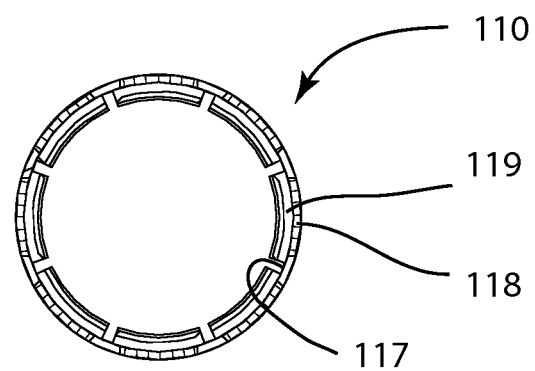
FIG. 12C is an end cross-sectional view of the sleeve of FIG. 12A, taken at line B-B, showing inner flaps of the vents.

FIGS. 12A-12C shows sleeve 110 in greater detail. Sleeve 110 comprises at least one zone 116 which has a plurality of slot-like fenestrations 118 arrayed transverse to the longitudinal axis of the sleeve. Adjacent each fenestration 118 on an inner side 117 of the sleeve wall is a flap 119. When no pressure is applied through the lumen of the sleeve, the flaps 119 project radially inward, so that the vent-like fenestrations 118 are open. When fluid pressure is applied through the lumen, the pressure closes the flaps 119 so that they are substantially parallel to the inner side of the sleeve, covering and closing the fenestrations 118. If a sleeve 110 is placed in a vessel so that second zone 116 is adjacent an aneurysm neck and blood is allowed to flow through the sleeve, the flaps 119 will be held closed by the blood flow, preventing flow into the aneurysm. If the second zone 116 overlaps any branching vessels, perpendicular flow should open the flaps to minimize disruption of flow to those vessels. The round fenestrations 112 in zones 114 may also allow blood flow to adjacent branching vessels in those zones. The flaps 119 may comprise a polyurethane film or equivalent. Sleeve 110 may be used by itself, formed into a stent such as stent 70, or used with a stent such as stent 70. Zone 116 may be circumferential as in FIGS. 12A-12C, or may occupy a round, rectangular or other shaped portion of the sleeve.

Figure 13A:
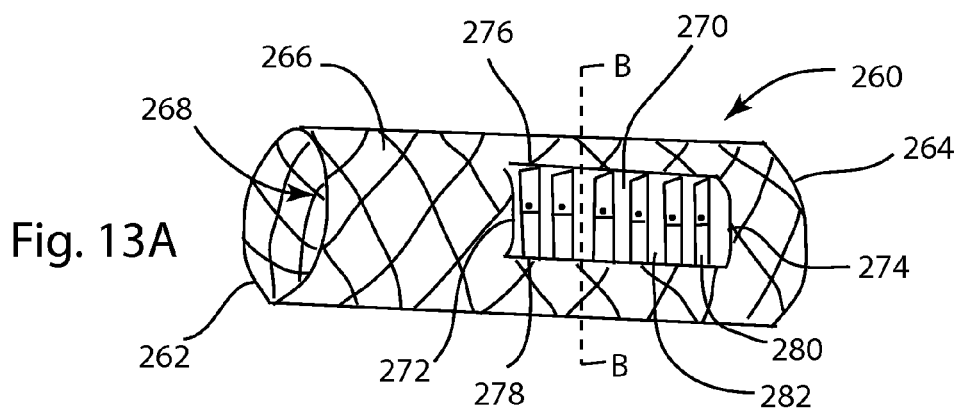
FIG. 13A is a perspective view of a stent comprising a window having pivotable flaps which are selectively actuable to open or close.
Figure 13B:
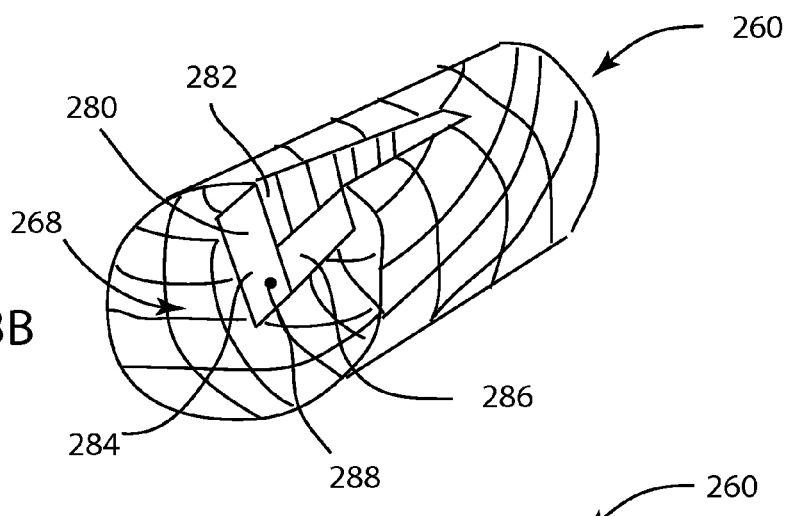
FIG. 13B is a cross-sectional view of the stent of FIG. 17A taken at line B-B, the stent in a compact configuration.
Figure 13C:
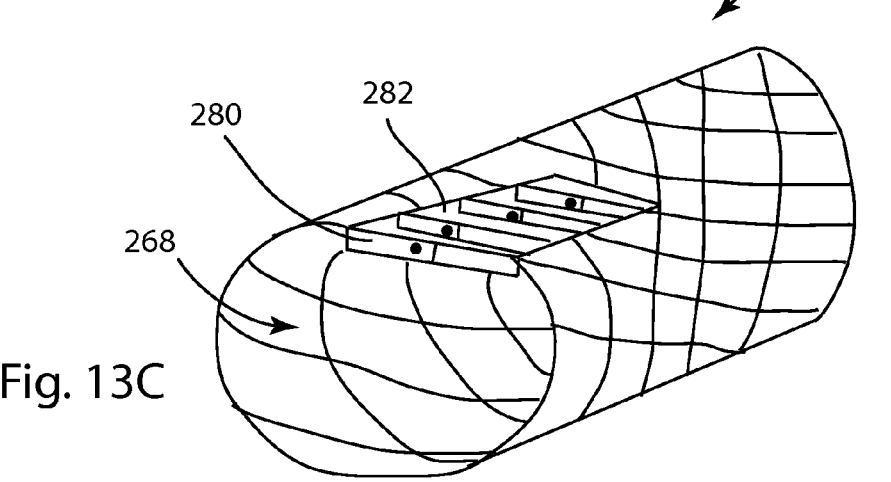
FIG. 13C is a cross-sectional view of the stent of FIG. 17A taken at line B-B, the stent in an expanded configuration.

FIGS. 13A-C and 14A-B illustrate an embodiment of a flexible, expandable stent comprising a window portion which may be selectively actuated to partially or totally occlude blood flow through the window portion. Stent 260 comprises a first end 262, a second end 264, and a stent wall 266 which defines a lumen 268. A portion of the stent wall comprises a window portion 270 defined by a first end 272, a second end 274, and first 276 and second 278 sides. As the stent is flexible and expandable, the window is expandable from a compact configuration as seen in FIG. 13B to an expanded configuration as seen in FIGS. 13A and 13C. In the compact configuration, the first and second sides are relatively close together and may touch or overlap, while in the expanded configuration they are spaced apart from one another. Extending across the window from the first side 276 to the second side 278 are a plurality of flaps 280 interposed with a plurality of vent openings 282. Each flap 280 may comprise a first flap segment 284 and a second flap segment 286, coupled together by a hinge or pivot 288. In other embodiments, each flap may comprise a unitary piece, similar to flap 119 in FIG. 12B. Because flaps 280 comprise a pivot, the first and second flap segments may pivot relative to one another about the pivot to increase or decrease the width of the window portion.

Figure 14A:
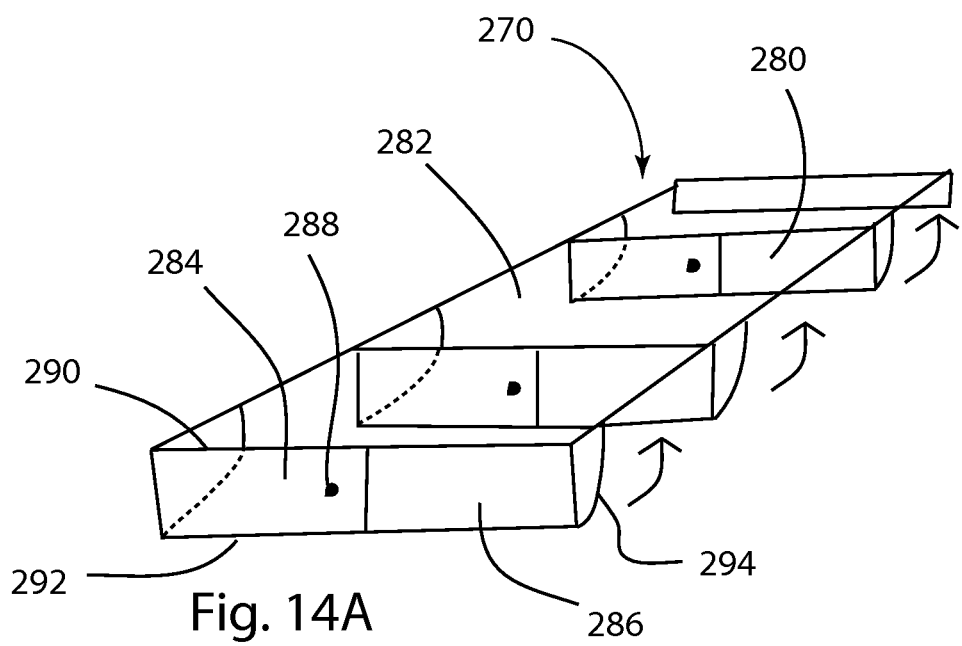
FIG. 14A is a detail view of the window of FIG. 17A, with the flaps in an open position.
Figure 14B:
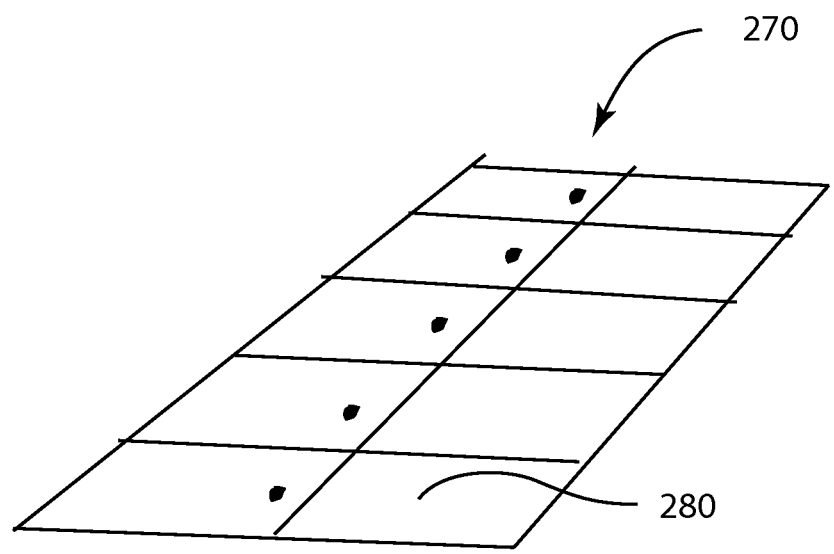
FIG. 14B is a detail view of the window of FIG. 17A, with the flaps in a closed position.
Figure 16:
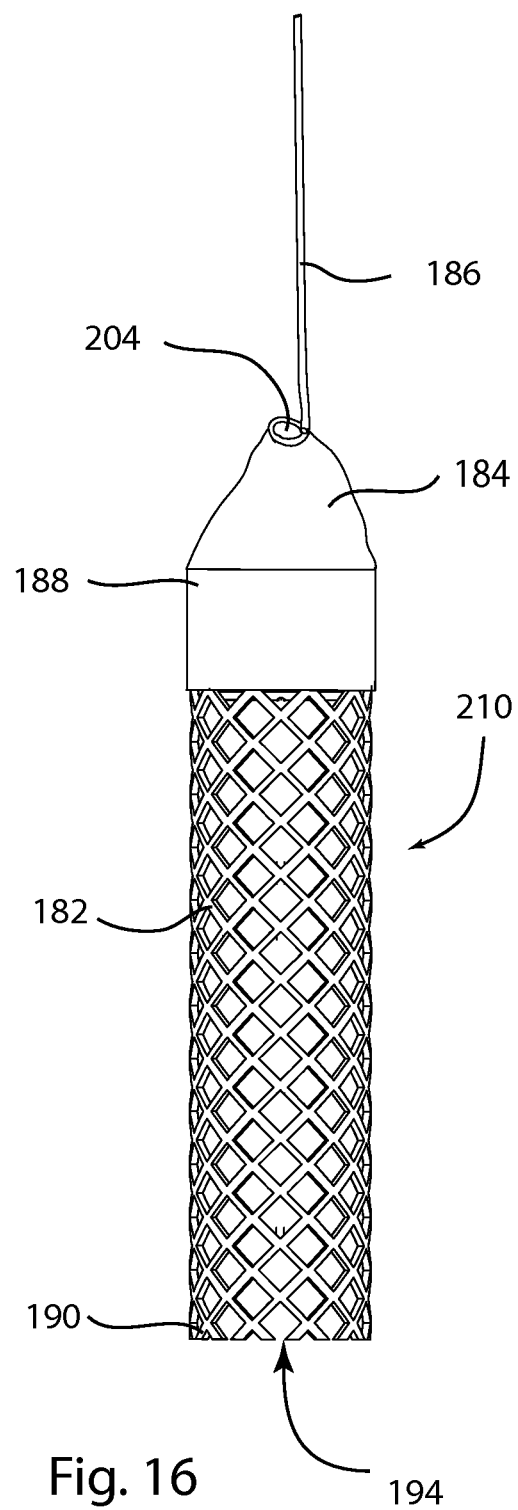
FIG. 16 is a side view of an alternate embodiment of an intra-luminal occlusion device with a sheath orifice in a partially open configuration.

FIGS. 14A and 14B illustrate the window portion in more detail. Referring to FIG. 14A, in an open window configuration, the flaps are substantially orthogonal to the stent wall (also seen in FIG. 17C). Each flap segment 288 has a first edge 290 and a second edge 292, which may define a top and bottom of the flap. An actuating mechanism comprising a tether 294 may be connected to each flap segment 284, 286. The tethers may be collectively actuated to pivot the flap segments about their first edges, moving the second edges along the direction of the arrows, to transform the window from the open window configuration seen in FIG. 14A and FIG. 13C, to a closed window configuration seen in FIG. 14B, and vice versa. In the closed window configuration, the flaps have been pivoted approximately 90° so that the first edge of one flap is adjacent to or overlies the first edge of the immediately adjacent flap, effectively closing the interposing vent 282. The tethers may be connected to one another such that actuating a single tether or actuating mechanism pivots all the flaps, similar to opening and closing the slats on a venetian blind by pulling a single cord, or collapsing a row of standing dominoes by touching one domino.

Referring again to FIG. 13A, stent 260 may be implanted in a vessel adjacent an aneurysm, with window 270 adjacent the aneurysm neck. Window 270 may be opened to allow introduction of a coil or other vaso-occlusive device into the aneurysm, then closed, to prevent migration of the coil and prevent blood flow into the aneurysm. The window 270 may further comprise a locking mechanism or fastening that retains the window in the closed configuration. The window may be sized and shaped to occupy only the portion of the stent wall that is adjacent the aneurysm neck, and the remainder of the stent wall may allow unimpeded blood flow. Thus, any branching vessels near the aneurysm will not be occluded when the window is closed.

Devices for intra-luminal occlusion of blood flow are illustrated in FIGS. 15A-15D and 16. Flow occlusion device 180 comprises a stent portion 182, expandable occlusion sheath 184, and an actuating portion which comprises a cable or drawstring 186. Stent portion 182 may comprise a flexible, expandable stent, having a first end 188, a second end 190 and a stent wall 192 defining a stent lumen 194. Attached to the first end 188 is the expandable occlusion sheath 184. Sheath 184 may comprise a tubular portion of flexible, compliant material which may comprise nylon, polyester, polyurethane, polyvinyl chloride, Teflon, ePTFE, PTFE, polyethylene, polypropylene, silicone, PEEK, and/or hydrogel, among others. The sheath may comprise mesh in which fibers are knitted, woven, braided, or otherwise intermeshed together. The sheath 184 comprises a first end 196, a second end 198, and a sheath lumen 200 defined by a sheath wall 202. A sheath orifice 204 is defined by the second end 198. The first end 196 of the sheath is attached to the first end 188 of the stent, and in the open configuration illustrated in FIG. 15B, the sheath lines a portion of the stent lumen 194 adjacent the first end 188 of the stent, with the second end 198 of the sheath oriented toward the second end 190 of the stent 182. The second end 198 of the sheath slidingly engages the drawstring 186, which extends through the stent lumen 194, such that a first end 187 of the drawstring 186 lies outside the second end 190 of the stent 182.

As the drawstring first end 187 is pulled axially relative to the stent, the second end 198 of the sheath is drawn closed, gradually closing the sheath orifice 204. The sheath orifice 204 may be substantially circular in shape; as the second end 198 of the sheath is drawn closed, the diameter of the sheath orifice decreases.

To effect partial or complete occlusion of a blood vessel, flow occlusion device 180 may be implanted in the vessel at a desired location. As long as the sheath orifice remains open, as in FIG. 15B, blood may flow freely through the vessel. Partial occlusion of the vessel may be accomplished by pulling the drawstring 186 to draw the sheath second end 198 partially closed, thus decreasing the size of the sheath orifice 204, as seen in FIG. 15C. If complete occlusion of the vessel is desired, drawstring 186 may be pulled to drawn the sheath second end 198 entirely closed, thus closing the sheath orifice 204. When the sheath orifice 204 is partially or completely closed, flow pressure may cause the sheath may inflate or swell like a fluid filled parachute or balloon, as seen in FIG. 15D. The flow occlusion device 180 may also be self-opening via a self-expanding ring in the sheath second end 198, which may be comprised of Nitinol, stainless steel, or any other previously mentioned materials, such that the sheath orifice 204 is increased in size in response to a relaxation of tension on the drawstring 186. It is anticipated that the drawstring 186 would extend through the proximal vasculature and out of the body through a vascular port to a tie-off location or dial. This functionality allows the clinician to apply tension or remove tension over a period of time to adjustably control flow through the flow occlusion device 180 and perhaps allow collateral circulation to take develop in response to the vessel occlusion.

In an alternate embodiment of a flow occlusion device, the sheath 184 and the drawstring 186 are not be positioned to extend back through the stent lumen 194 toward the stent second end 190, but instead extend axially away from the first end 188 of the stent in the opposite direction. See FIG. 16, which illustrates flow occlusion device 210 in a mostly closed configuration.

In another alternate embodiment of a flow occlusion device, the occlusion sheath may be replaced with a plurality of sheets, membranous scales or plate-like members, connected to an actuating member. The actuation member may be actuated to close the plate-like members around the orifice, functioning similar to the iris of a camera lens to gradually close the orifice, occluding blood flow.

Figure 18:
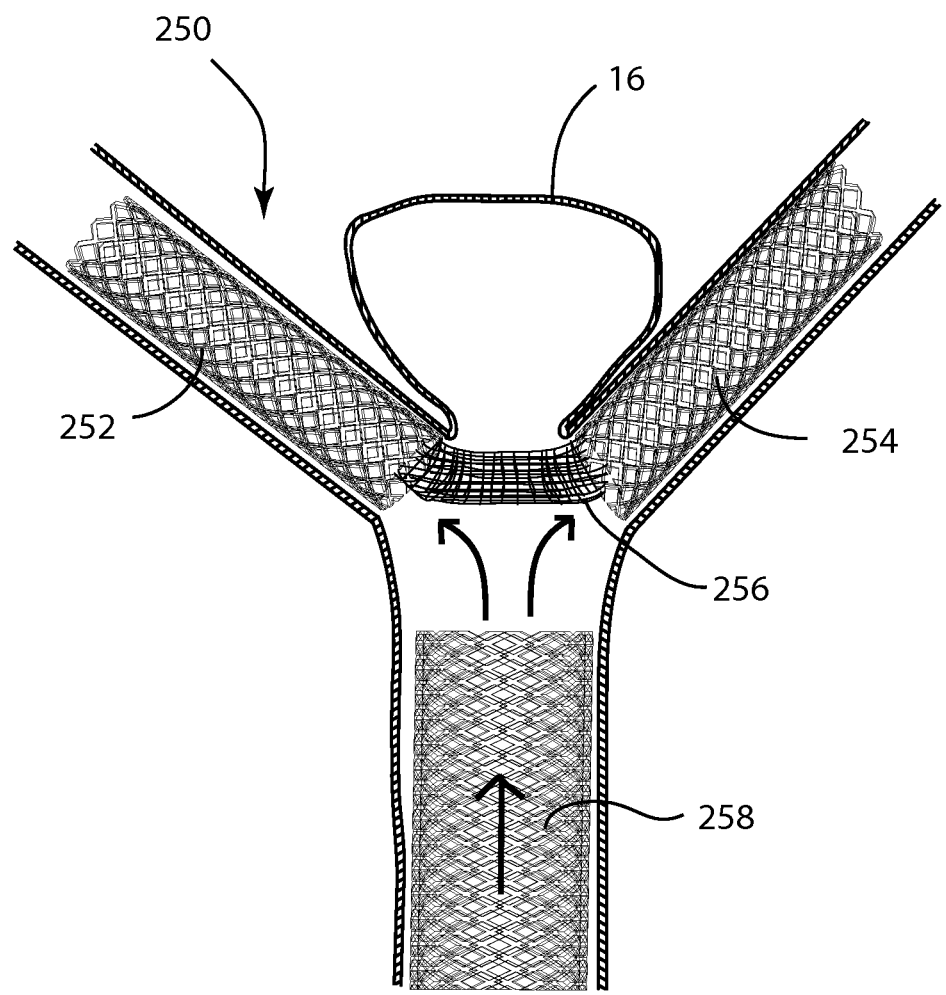
FIG. 18 is a partial cross-sectional view of a basilar tip aneurysm, with two stents in adjacent branching vessels and a connection mesh bridging the aneurysm and connecting the two stents, and a third stent in a main vessel.

Referring to FIGS. 17-18, devices for aneurysm treatment comprising stent portions coupled with connection mesh portions are shown. In FIG. 17A, aneurysm treatment device 220 comprises a first stent segment 222 having a first end 224 and second end 226, second stent segment 228 having a first end 230 and second end 232, and connection mesh 234 having a first mesh end 236 and a second mesh end 238. The connection mesh 234 is coupled to the first end 224 of the first stent segment 222, and the second end 232 of the second stent segment 228. The connection mesh is sized and shaped to form a half-pipe or half-cylinder between the two substantially cylindrical stent segments; and sized to completely bridge the neck of wide-necked aneurysm 8, the cutaway portion of which is indicated by a dashed line. The connection mesh is shown as attached to the stent segments at their ends; however in other embodiments the connection mesh could overlap portions of one or both stent segments. A coil 40 or other vaso-occlusive member may be introduced into the aneurysm prior to or after placement of the device 220, or the device may be used alone.

The connection mesh may comprise a portion of woven, knitted, braided, or otherwise intermeshed fibers. The fibers may comprise nylon, Nitinol, Dacron, polyester, polyurethane, polyvinyl chloride, Teflon, ePTFE, PTFE, polyethylene, polypropylene, silicone, PEEK, and/or hydrogel, among others. As seen in FIG. 17A, the mesh may form a half-cylinder of 180°, or it may subtend an angle ranging from 30° to a full cylinder of 360°, as shown in FIG. 17B illustrating an aneurysm treatment device 240 comprising connection mesh 242.

Referring to FIG. 18, an aneurysm treatment device 250 may be placed to bridge the neck of a Y-junction vascular aneurysm, such as a basilar tip aneurysm 16. Device 250 comprises a first stent segment 252 and second stent segment 254, connected by connection mesh 256. Connection mesh 256 may be sized and shaped as a half-pipe or other partial cylinder, to prevent blood flow from entering the aneurysm and deflect blood flow through stent segments 252 and 254, as illustrated by arrows in FIG. 18. Optionally, a third stent segment 258 may be placed in the main vessel to reinforce it or encourage flow to divert into stent segments 252 and 254 and away from aneurysm 16. A baffle may also be formed into the connection mesh 256 to further divert blood flow into the branching vessels and away from the aneurysm 16.

The present invention may be embodied in other specific forms without departing from its spirit or essential characteristics. For example, above are described various alternative examples of systems for providing aneurysm treatment or vessel occlusion. It is appreciated that various features of the above-described examples can be mixed and matched to form a variety of other alternatives. For example, a barrier member or stent may be implanted with or without a vaso-occlusive coil or balloon. Variations in fenestration or cell opening sizes, shapes and distribution may occur on inner sleeves and/or outer stents. Sleeves and stents can be juxtaposed in positional relationship or integrated into one component. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for treating an aneurysm in a parent vessel, the parent vessel defining a lumen and having a lumen wall, the aneurysm having a neck communicating with the lumen, the system comprising:
   a flexible stent configured for placement in the parent vessel adjacent the aneurysm neck, the stent comprising a first end and a second end and a stent wall extending therebetween defining a stent bore, the stent wall permeable to blood flow, the stent wall comprising a plurality of stent cells;
   an inner sleeve positioned inside and coaxial with the flexible stent, the inner sleeve comprising a first end and a second end and a sleeve wall extending therebetween defining a sleeve bore, the sleeve wall comprising a plurality of sleeve cells; and
   an implantable barrier device configured for placement within the aneurysm neck, the barrier device positioned outside of the stent and adjacent to the stent, the barrier device formed as a disc-shaped member having a first side and a second side opposite the first side, the barrier device comprising a first compact configuration and a second expanded configuration, the barrier device impermeable to blood flow in the second expanded configuration, wherein in the second expanded configuration, the barrier device is shaped to extend across the aneurysm neck to prevent blood flow through the aneurysm neck;
   a vaso-occlusive device positioned outside the stent and adjacent the barrier device, the barrier device between the vaso-occlusive device and the stent, wherein when the vaso-occlusive device is in the aneurysm and the barrier device is extended across the aneurysm neck in the second expanded configuration, the barrier device retains the vaso-occlusive device within the aneurysm
   wherein the vaso-occlusive device comprises a balloon comprise-sing an elastomeric sheath having a plurality of zones, the zones having varying levels of elasticity.

2. The system of claim 1, wherein the barrier device is configured to radially expand from the first compact configuration to the second expanded configuration.

3. The system of claim 1, wherein the barrier device is configured to unroll or unfold from the first compact configuration to the second expanded configuration.

4. The system of claim 1, wherein the barrier device comprises a fiber mesh, the fiber mesh comprising strands chosen from the group consisting of: nylon, polypropylene, polyester, polyurethane, polyvinyl chloride, Teflon, ePTFE, PTFE, polyethylene, polypropylene, silicone, PEEK, and hydrogel.

5. The system of claim 1, wherein the barrier device is connected to the vaso-occlusive device, and wherein the barrier device and the vaso-occlusive device are configured to be deliverable together through a microcatheter.

6. A system for treating an aneurysm in a parent vessel, the parent vessel defining a lumen and having a lumen wall, the aneurysm having a neck communicating with the lumen, the system comprising:
   a flexible stent configured for placement in the parent vessel adjacent the aneurysm neck, the stent comprising a first end and a second end and a stent wall extending therebetween defining a stent bore, the stent wall permeable to blood flow, the stent wall comprising a plurality of stent cells, the stent further comprising a stent window located in the stent wall;
   an inner sleeve positioned inside and coaxial with the flexible stent, the inner sleeve comprising a first end and a second end and a sleeve wall extending therebetween defining a sleeve bore, the sleeve wall comprising a plurality of sleeve cells; and
   an implantable barrier device configured for placement within the aneurysm neck, the barrier device positioned outside of the stent and adjacent to the stent, the barrier device formed as a disc-shaped member having a first side and a second side opposite the first side, the barrier device comprising a first compact configuration and a second expanded configuration, the barrier device impermeable to blood flow in the second expanded configuration;
   wherein in the second expanded configuration, the barrier device is shaped to extend across the aneurysm neck to prevent blood flow through the aneurysm neck.

7. The system of claim 6, wherein the sleeve further comprises a sleeve window located in the sleeve wall.

8. The system of claim 7, wherein the system comprises a closed configuration in which the sleeve window is offset from the stent window so that no portion of the sleeve window overlaps the stent window.

9. The system of claim 8, wherein the system further comprises an open configuration in which the sleeve window is aligned with the stent window, forming an unimpeded opening through the stent wall and the sleeve wall.

10. The system of claim 9, wherein the sleeve rotates relative to the stent to transform the system between the open configuration and the closed configuration.

11. A system for treating an aneurysm in a parent vessel, the parent vessel defining a lumen and having a lumen wall, the aneurysm having a neck communicating with the lumen, the system comprising:
   a flexible stent configured for placement in the parent vessel adjacent the aneurysm neck, the stent comprising a first end and a second end and a stent wall extending therebetween defining a stent bore, the stent wall permeable to blood flow, the stent wall comprising a plurality of stent cells, a stent window located in the stent wall;
   an inner sleeve positioned inside and coaxial with the flexible stent, the inner sleeve comprising a first end and a second end and a sleeve wall extending therebetween defining a sleeve bore, the sleeve wall comprising a plurality of sleeve cells, a sleeve window located in the sleeve wall;
   wherein the system comprises an open configuration in which the sleeve window is aligned with the stent window, forming an unimpeded opening through the stent wall and the sleeve wall; and
   wherein the system comprises a closed configuration in which the sleeve window is offset from the stent window so that no portion of the sleeve window overlaps the stent window.

12. The system of claim 11, wherein the vaso-occlusive device is a coil.

13. The system of claim 11, wherein the sleeve cells are differently shaped than the stent cells.

14. The system of claim 11, the system further comprising a vaso-occlusive device configured to be deployed inside the aneurysm, wherein the vaso-occlusive device is positioned outside the stent.

15. The system of claim 14, wherein the system is in the closed configuration, wherein the stent window is positioned between the sleeve wall and the vaso-occlusive device.

16. The system of claim 14, the system further comprising an expandable barrier configured for placement within the aneurysm neck, the expandable barrier comprising a first compact configuration and a second expanded configuration, the expandable barrier positioned between the stent and the vaso-occlusive device.

17. The system of claim 16, wherein the expandable barrier is positioned outside the sleeve wall, and the stent window is positioned between the sleeve wall and the expandable barrier.

18. The system of claim 16, wherein the vaso-occlusive device is coupled to the expandable barrier to be deployed with the expandable barrier.

19. The system of claim 16, wherein the expandable barrier comprises an anchor.

20. The system of claim 16, wherein the expandable barrier is disc-shaped, the expandable barrier comprising an outer side, an inner side and a stem.

21. The system of claim 20, wherein the outer side is coupled to the stem, and the stem is slidable relative to the inner side to transform the expandable barrier between the first compact configuration and the second expanded configuration.

* * * * *

UNITED STATES PATENT AND TRADEMARK OFFICE
CERTIFICATE OF CORRECTION

PATENT NO. : 8,470,013 B2  
APPLICATION NO. : 12/582052  
DATED : June 25, 2013  
INVENTOR(S) : Duggal et al.

It is certified that error appears in the above-identified patent and that said Letters Patent is hereby corrected as shown below:

In the Claims:

Column 16, line 22, Claim 12, cancel the text beginning with "12. The system of" and ending "the vaso-occlusive device." and the following claims should read:

Column 16, line 22, Claim 12:
12. The system of claim 11, wherein the sleeve cells are differently shaped than the stent cells.

Column 16, lines 24-25, Claim 13:
13. The system of claim 11, the system further comprising a vaso-occlusive device configured to be deployed inside the aneurysm, wherein the vaso-occlusive device is positioned outside the stent.

Column 16, lines 26-27, Claim 14:
14. The system of claim 13, wherein the system is in the closed configuration, wherein the stent window is positioned between the sleeve wall and the vaso-occlusive device.

Column 16, line 28, Claim 15:
15. The system of claim 13, wherein the vaso-occlusive device is a coil.

Column 16, line 29-31, Claim 16:
16. The system of claim 13, the system further comprising an expandable barrier configured for placement within the aneurysm neck, the expandable barrier comprising a first compact configuration and a second expanded configuration, the expandable barrier positioned between the stent and the vaso-occlusive device.

Signed and Sealed this  
Third Day of September, 2013

Teresa Stanek Rea  
*Acting Director of the United States Patent and Trademark Office*